(12) United States Patent
Zipfel et al.

(10) Patent No.: US 8,232,452 B2
(45) Date of Patent: Jul. 31, 2012

(54) METHODS, MEANS AND COMPOSITIONS FOR ENHANCING AGROBACTERIUM-MEDIATED PLANT CELL TRANSFORMATION EFFICIENCY

(75) Inventors: Cyril Zipfel, Norwich (GB); Jonathan Dallas George Jones, Norwich (GB); Dagmar Renate Hann, Norwich (GB); John Paul Rathjen, Norwich (GB)

(73) Assignee: Plant Bioscience Limited, Colney Lane, Norwich (GB)

( * ) Notice: Subject to any disclaimer, the term of this patent is extended or adjusted under 35 U.S.C. 154(b) by 793 days.

(21) Appl. No.: 12/097,256

(22) PCT Filed: Dec. 15, 2006

(86) PCT No.: PCT/GB2006/004688
§ 371 (c)(1),
(2), (4) Date: Jun. 12, 2008

(87) PCT Pub. No.: WO2007/068935
PCT Pub. Date: Jun. 21, 2007

(65) Prior Publication Data
US 2008/0307539 A1    Dec. 11, 2008

(30) Foreign Application Priority Data
Dec. 16, 2005 (GB) .................................. 0525645.8

(51) Int. Cl.
*A01H 5/00* (2006.01)
*A01H 1/00* (2006.01)
*C12N 15/09* (2006.01)
*C12N 1/20* (2006.01)

(52) U.S. Cl. ........ 800/278; 800/294; 800/298; 800/306; 435/468; 435/252.2

(58) Field of Classification Search .................. None
See application file for complete search history.

(56) References Cited

U.S. PATENT DOCUMENTS

| | | | |
|---|---|---|---|
| 6,162,965 A * | 12/2000 | Hansen ......................... | 800/278 |
| 6,444,470 B1 | 9/2002 | Ross et al. | |
| 2003/0233676 A1 * | 12/2003 | Tzfira et al. .................. | 800/279 |
| 2005/0060777 A1 | 3/2005 | Lopez-Molina et al. | |

FOREIGN PATENT DOCUMENTS

WO    WO/98/54961 A    12/1998

OTHER PUBLICATIONS

Veena et al. The Plant Journal (2003) 35:219-236.*
Daveltova, Sholpan et al, "The zinc-finger protein Zat12 plays a central role in reactive oxygen and abiotic stress signaling in *Arabidopsis*," Plant Physiology, Oct. 2005, pp. 847-856, vol. 139, No. 2, Rockville.
Ditt, R. F. et al, "The plant cell defense and *Agrobacterium tumefaciens*," Fems Microbiology Letters, Jun. 15, 2005, pp. 207-213, vol. 247, No. 2, Amsterdam.
Veena et al, "Transfer of T-DNA and Vir proteins to plant cells by *Agrobacterium tumefaciens* induces expression of host genes involved in mediating transformation and suppresses host defense gene expression," Plant Journal, Jul. 2003, pp. 219-236, vol. 35, No. 2.
Ton, Jurriaan et al, "Beta-amino-butyric acid-induced resistance against necrotrophic pathogens is based on ABA-dependent priming for callose," Plant Journal, Apr. 2004, pp. 119-130, vol. 38, No. 1.
Yun, Maximina H. et al, "Xanthan induces plant susceptibility by suppressing calllose deposition," Plant Physiology, May 2006, pp. 178-187, vol. 141, No. 1, Rockville.
Ditt, Renata F. et al, "Plant gene expression response to *Agrobacterium tumefaciens*," Proceedings of the National Academy of Science of the United States of America, Sep. 11, 2001, pp. 10954-10959, vol. 98, No. 19.
Escobar, Matthew A. et al, "*Agrobacterium tumefaciens* as an agent of disease," Trends in Plant Science, Aug. 2003, pp. 380-386, vol. 8, No. 8.
Nurnberger, Thorstein et al, "Innate immunity in plants and animals: striking similarities and obvious differences," Immunological Reviews Apr. 2004, pp. 249-266, vol. 198.
Zipfel, C et al, "Plants and animals: A different taste for microbes?" Current Opinion in Plant Biology, Aug. 2005, pp. 353-360, vol. 8, No. 4, Quadrant Subscription Services, Great Britain.
Oh, Hye-Sook et al, "Basal resistance against bacteria in *Nicotiana benthamiana* leaves is accompanied by reduced vascular staining and suppressed by multiple *Pseudomonas* syringe type III secretion system effector proteins," Plant Journal, Oct. 2005, pp. 348-359, vol. 44, No. 2.
Abramovitch, Robert B. et al, "Strategies used by bacterial pathogens to suppress plant defenses," Current Opinion in Plant Biology, pp. 356-364, vol. 7, No. 4.
Lamb, C. J. et al, "Signals and transduction mechanisms for activation of plant defenses against microbial attack," Cell, 1989, pp. 215-224, vol. 56, No. 2.
Puonti-Kaerlas, J. "International Search Report and Written Opinion," Jun. 15, 2007, for PCT/GB2006/004688 filed on Dec. 15, 2006.

* cited by examiner

*Primary Examiner* — Medina A Ibrahim
(74) *Attorney, Agent, or Firm* — Janet Smith; Speckman Law Group PLLC

(57) ABSTRACT

Higher eukaryotes sense microbes through perception of pathogen-associated molecular patterns (PAMPs). The flagellin receptor FLS2 represents so far the only known pattern recognition receptor (PRR) in *Arabidopsis*. *Arabidopsis* plants detect a variety of PAMPs including specific epitopes of the bacterial proteins flagellin and EF-Tu. Here, we show that flagellin and EF-Tu activate a common set of signalling events and defence responses, but without clear additive or synergistic effects. Treatment with either PAMP results in increased receptor sites for both PAMPs, a finding employed in a reverse-genetic approach to identify the receptor kinase EFR as the EF-Tu receptor. Transient expression of EFR in *Nicotiana benthamiana* results in formation of specific binding sites for EF-Tu, and responsiveness to this PAMP. *Arabidopsis* efr mutants show a higher frequency of T-DNA transformation by the bacterium *Agrobacterium tumefaciens*, revealing a role for EF-Tu perception in restricting this plant pathogen. These results demonstrate that EFR is the receptor for EF-Tu and that plant defence responses induced by PAMPs like EF-Tu reduce transformation by *Agrobacterium*.

14 Claims, 16 Drawing Sheets

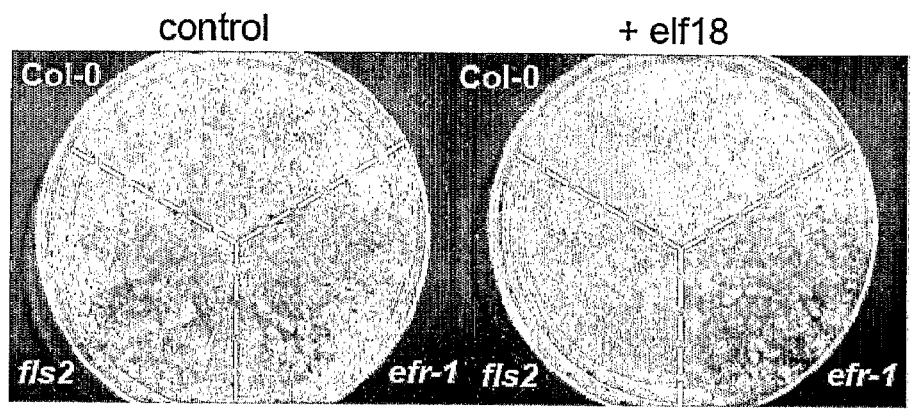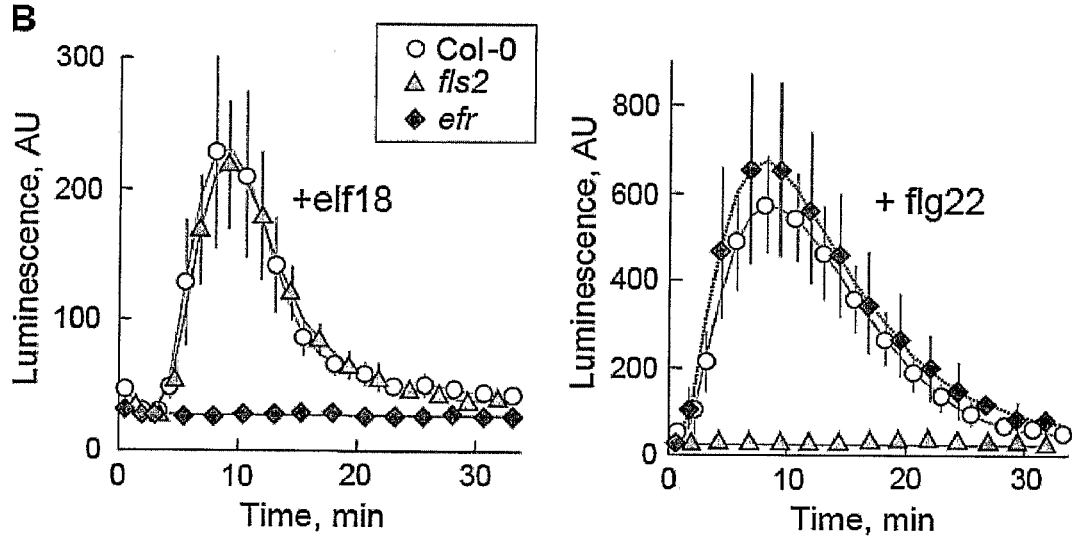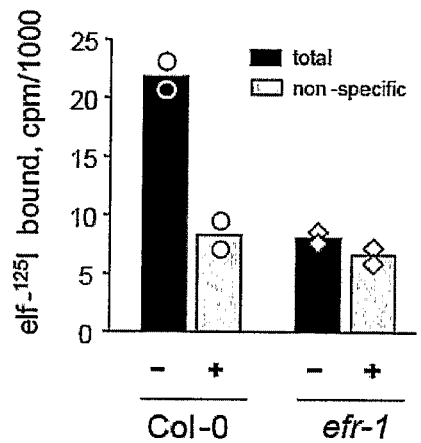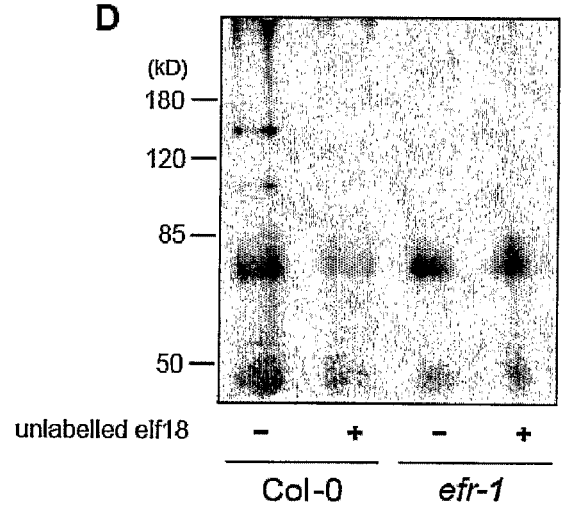
FIGURE 4

A

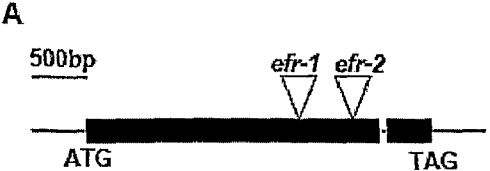

B

| | |
|---|---|
| signal peptide | 1<br>MKLSFSLVFNALTLLLQVCIFAQA |
| N-terminus | 25<br>RFSNETDMQALLEFKSQVSENNKRE<br>VLASWNHSSPFCNWIGVTCGRRR<br>VISLNLGGFKLTGVISPSIGN |
| LRR domain | 96<br>LSFLRLLNLADNSFGSTIPQKVGR<br>LFRLQYLNMSYNLLEGRIPSSLSN<br>CSRLSTVDLSSNHLGHGVPSELGS<br>LSKLAILDLSKNNLTGNFPASLGN<br>LTSLQKLDFAYNQMRGEIPDEVAR<br>LTQMVFFQIALNSFSGGFPPALYN<br>LSSLESLSLADNSFSGNLRADFGYL<br>LPNLRRLLLGTNQFTGATPKTLAN<br>LSSLERFDISSNYLSGSIPLSFGK<br>LRNLWWLGIRNNSLGNNSSSGLEFIGAVAN<br>CTQLEYLDVGYNRLGGELPASLANL<br>STTLTSLFLGQNLISGTIPHDLCN<br>LVSLQELSLETNMLSGELPVSFGK<br>LLNLQVVDLYSNAISGEIPSYFGN<br>MTRLQKLHLNSNSFHGRIPQSLGR<br>CRYLLDLWMDTNRLNGTIPQEILQ<br>LPSLAYIDLSNNFLTGHFPEEVGK<br>LELLVGLGASYNKLSGKMPQAIGG<br>CLSMEFLFMQGNSFDGATPDISR<br>LVSLKNVDFSNNNLSGRIPRYLAS<br>LPSLRNLNLSMQKFEGRVPTTGVF<br>LxxLxxLxLxxNxLxGxIPxxLGx |
| juxtamembrane,<br>extracellular | 607<br>RNATAVSVFGNTNICGGVREMQLKPC<br>IVQASPRKRKPLSV |
| transmembrane | 647<br>RKKVVSGICIGIASLLLIIIVASLCWFMKRKKK |
| juxtamembrane,<br>intracellular | 681<br>NNASDGNPSDSTTLGMFHEKVSYEELHSATSR |
| Ser/Thr protein<br>kinase domain | 712<br>FSSTNLIGSNFGNVFKGLLGPENKLVAVK<br>VLNLLKHGATKSFMAECETFKGIRHRNLV<br>KLITVCSSLDEGNDFRALVYEFMPKGSLD<br>MWLQLEDLERVNDHSRSLTPAEKLNIAID<br>VASALEYLHVHHDPVAHCDIKPSNILLDD<br>DLTAHVSDFGLAQLLYKYDRESFLNQFSS<br>AGVRGTIGYAAPYGMGGQPSIQGDVYSFG<br>ILLLEMFSGKEPTDESFAGDYNLHSYTKS<br>ILSGCTSSGGSNAIDEGLRLVLQVGIKCS<br>EEYPRDRMRTDEAVRELISIRSKFF |
| C-terminus | 1001<br>SSKTTITESPRDAPQSSPQEWMLNTDMHTM |

FIGURE 5

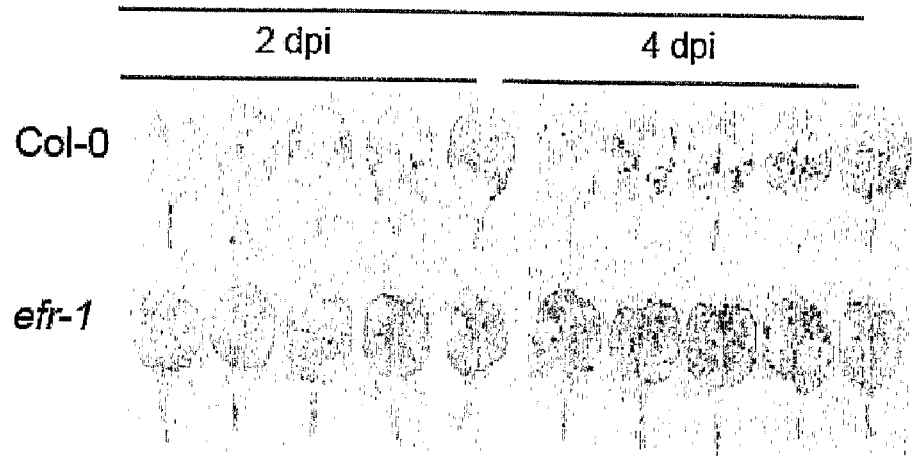
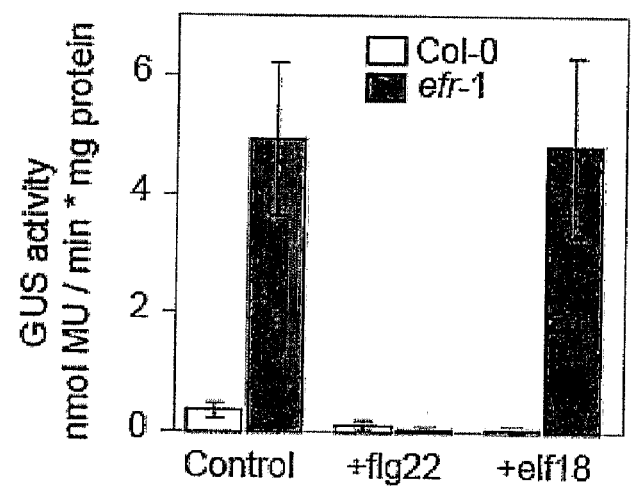
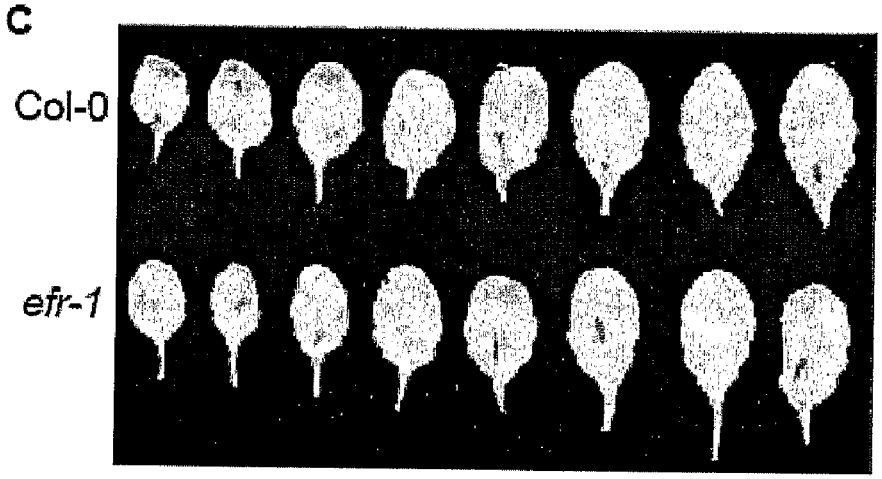
FIGURE 7

76R: PtabF
N.b.: PtabF
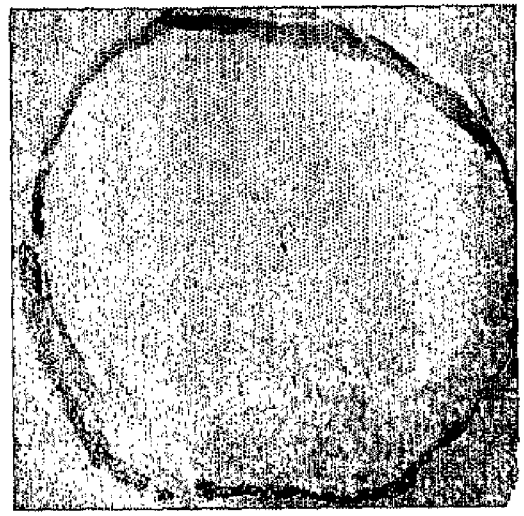
76R: PtomF
N.b.: PtomF
FIGURE 10

METHODS, MEANS AND COMPOSITIONS FOR ENHANCING AGROBACTERIUM-MEDIATED PLANT CELL TRANSFORMATION EFFICIENCY

REFERENCE TO RELATED APPLICATIONS

This application is the US national phase entry of International Patent Application No. PCT/GB2006/004688, filed Dec. 15, 2006, which claims priority to UK Patent Application No. 0525645.8, filed Dec. 16, 2005.

FIELD OF THE INVENTION

This invention relates to improved methods for achieving plant cell transformation.

BACKGROUND OF THE INVENTION

Activation of defence mechanisms in higher eukaryotes is dependent on an array of pattern recognition receptors (PRRs) which recognize molecular structures that are characteristic for microbes. These pathogen-associated molecular patterns (PAMPs) play key roles as activators of the innate immune response in animals (Medzhitov and Janeway, 2002; Akira and Takeda, 2004) and, analogously, as elicitors of defence responses in plants (Nornberger et al., 2004). In contrast to animals, plants have no specialized cells or organs for defence; rather, all cells can mount a defence response upon pathogen perception. Perception of pathogens by plants can be divided into three main phases which appear to reflect steps of co-evolution in plant-pathogen interaction (Nürnberger et al., 2004). In a first phase, perception of PAMPs or "general elicitors" by the host leads to rapid activation of defence mechanisms such as cell wall reinforcement by callose deposition and production of reactive oxygen species (ROS), and induction of numerous defence-related genes. In a second phase, virulence factors evolved by successful pathogens can inhibit these PAMP-elicited basal defences (Espinosa and Alfano, 2004; Nomura et al., 2005; Kim et al., 2005). In a third phase, in turn, certain plant cultivars have evolved resistance (R) proteins specialized to detect these pathogen-derived virulence factors or the effects caused by them. As a consequence of this R protein-dependent perception process these plants trigger full, irreversible defence resulting in local lesion of the tissue termed hypersensitivity response (HR) and arrest of pathogen spreading (Nimchuk et al., 2003; Jones and Takemoto, 2004).

PAMPs perceived by plants include structures characteristic for oomycetes like the cell wall β-glucan, the pep13 epitope conserved in cell wall transglutaminase and secreted lipotransfer proteins termed elicitins (Nürnberger et al., 2004). Plants can also perceive structures signalling the presence of true fungi like the cell wall polysaccharide chitin and the fungal sterol ergosterol. Similarly, plants have been reported to recognize structures characteristic for bacteria like lipopolysacharides (LPS), bacterial cold-shock protein (CSP), flagellin and EF-Tu (Nürnberger et al., 2004; Zipfel and Felix, 2005). Some of these PAMPs are only perceived by a narrow range of plant species, whereas others trigger defence responses in a very broad range of species. Typically, any given plant seems to have perception systems for several PAMPs characteristic of the same class of microorganism. For example, flagellin induces responses in plants belonging to many different orders, while perception of the additional bacterial PAMPs CSP and EF-Tu seems to be restricted to the orders of Solanales and Brassicales, respectively.

Whereas many microbial patterns can act as PAMPs in plants, the corresponding PRRs remain largely unknown. So far, receptor binding sites have been reported only for a few examples, notably for heptaglucan from oomycetes (Umemoto et al., 1997), fungal xylanase (Ron and Avni, 2004) and bacterial flagellin (Gómez-Gómez and Boller, 2000; Chinchilla et al., 2006). The *Arabidopsis* flagellin receptor FLS2 is a membrane bound receptor kinase with a leucine-rich repeat (LRR) domain facing the apoplast. As such, FLS2 is a member of the receptor like kinases (RLKs), a family comprising >600 members in *Arabidopsis* (Shiu et al., 2004). So far, only a few of these RLKs have been associated with specific functions but these examples clearly indicate that members of this large gene family function as receptors for many of the different extracellular signals perceived by plants (Dievart and Clark, 2003; Shiu et al., 2004). Similar to FLS2, some of the RLKs with unknown function might act as PRRs for other PAMPs such as EF-Tu.

The epitope of EF-Tu, which gets recognized by *Arabidopsis* is restricted to a small domain around the acetylated N-terminus of the mature protein. PAMP-activity of EF-Tu can be mimicked by synthetic peptides representing this N-terminus with a minimum of the first 18 amino acid residues, as in the peptides elf18 and elf26 (Kunze et al., 2004). These peptides are active at subnanomolar concentrations while shorter peptides comprising less than 18 residues exhibit lower activity, and elf12, a peptide with only 12 residues, is completely inactive as an inducer of responses. Interestingly, elf12 acts as a specific, competitive antagonist for EF-Tu, indicating that this peptide binds but does not activate the EF-Tu receptor (Kunze et al., 2004). All these characteristics of EF-Tu perception bear resemblance to the perception of flagellin by its receptor FLS2.

In a first aspect of this invention, we demonstrate that EF-Tu binds to specific, high-affinity receptor binding sites distinct from FLS2 but elicits a set of defence response that is highly similar to that induced by flagellin.

In a second aspect of this invention, we screened T-DNA insertion lines for various FLS2-related RLKs and identified EFR (EF-Tu Receptor) as required for perception of EF-Tu in *Arabidopsis*. *Nicotiana benthamiana* plants have no perception system for EF-Tu, but gained capacity to respond to this PAMP when expressing EFR.

In a third aspect of this invention, we demonstrate that mutants lacking EF-Tu perception are more susceptible to transformation by *Agrobacterium tumefaciens*, thus revealing the functional importance of this perception system for plant defence. Furthermore, this result suggests that differences in sensing PAMPs exposed by *A. tumefaciens* might explain the pronounced differences in susceptibility to transformation by this bacterium observed between different plant species.

In other aspects, it is demonstrated that inhibitors of callose deposition, such as xanthan gum and 2-deoxy-D-Glucose (2-DDG) can increase the efficiency of *A. tumefaciens*-mediated transient expression.

Other aspects of this invention will be apparent from a review of the full disclosure and the claims appended hereto.

(A) Binding kinetics of the radiolabeled elf26-derivative elf-125I to intact cells of *Arabidopsis*. Cells were incubated with elf-$^{125}$I in the absence (shaded circles) or presence of 10 µM elf26-Tyr-Cys added at t=0 min (open triangles) or at 25 min (solid triangles). Radioactivity retained on the cells was measured by γ-counting after washing the cells on filters. Kinetics of binding was reproducible in four independent series of experiments with different batches of cells.

(B) Saturation of binding. Aliquots of cell suspension were incubated with different amounts of elf-$^{125}$I (specific activity diluted to 200 Ci/mmol with non-radioactive elf26-Tyr-Cys) at 4° C. for 25 min in the absence (total binding, shaded circles) or in the presence of 10 µM Tyr-elf26 (non-specific binding, open triangles). The values for specific binding (total binding minus non-specific binding, closed diamonds) fitted to rectangular hyperbola (solid line) resulted in a $B_{max}$ of 2.1 µmol/g cells and a $K_d$ of 0.8 nM. Values for saturation were reproduced in an independent saturation assay with a different batch of cells.

(C) Specificity of elf-$^{125}$I binding. Binding assays with elf-$^{125}$I and various concentrations of unlabeled flg22 and elf-derived peptides elf18, elf26, elf26-Pst and elf12. Results were obtained with different batches of Arabidopsis cells and are presented as percentage of specific binding in the absence of competitor. Total binding for these different batches was between 8,000 and 12,000 cpm, and non-specific binding was between 150 and 300 cpm. Competition of binding was tested for all competitors at least twice in independent assays.

(D) Chemical crosslinking of elf-$^{125}$I to Arabidopsis cells. After binding of elf-$^{125}$I in the presence of different concentrations of unlabeled elf26, crosslinking was initiated by the addition of EGS. Radiolabeled proteins were analyzed by SDS-PAGE and autoradiography on a Phosphor Imager. Numbers and dashes at right denote positions and molecular masses (Mr) in kilodaltons (kD) of standard proteins. Equal loading of proteins was checked by Coomassie-staining of the gel (not shown).

(E) Quantitative analysis of radioactivity in the band migrating at 150 kD band in (D). Radioactivity expressed as integration units (iu) obtained from the Phosphor Imager.

(F) Chemical crosslinking of elf-$^{125}$I and $^{125}$I-flg to Arabidopsis cells. Aliquots of Arabidopsis cells were supplied with $^{125}$I-flg and/or elf-$^{125}$I either alone, or with an excess of unlabeled flg22 or elf18 peptide as indicated. Crosslinking and analysis of radiolabeled proteins was performed as in (D).

Figure 1:
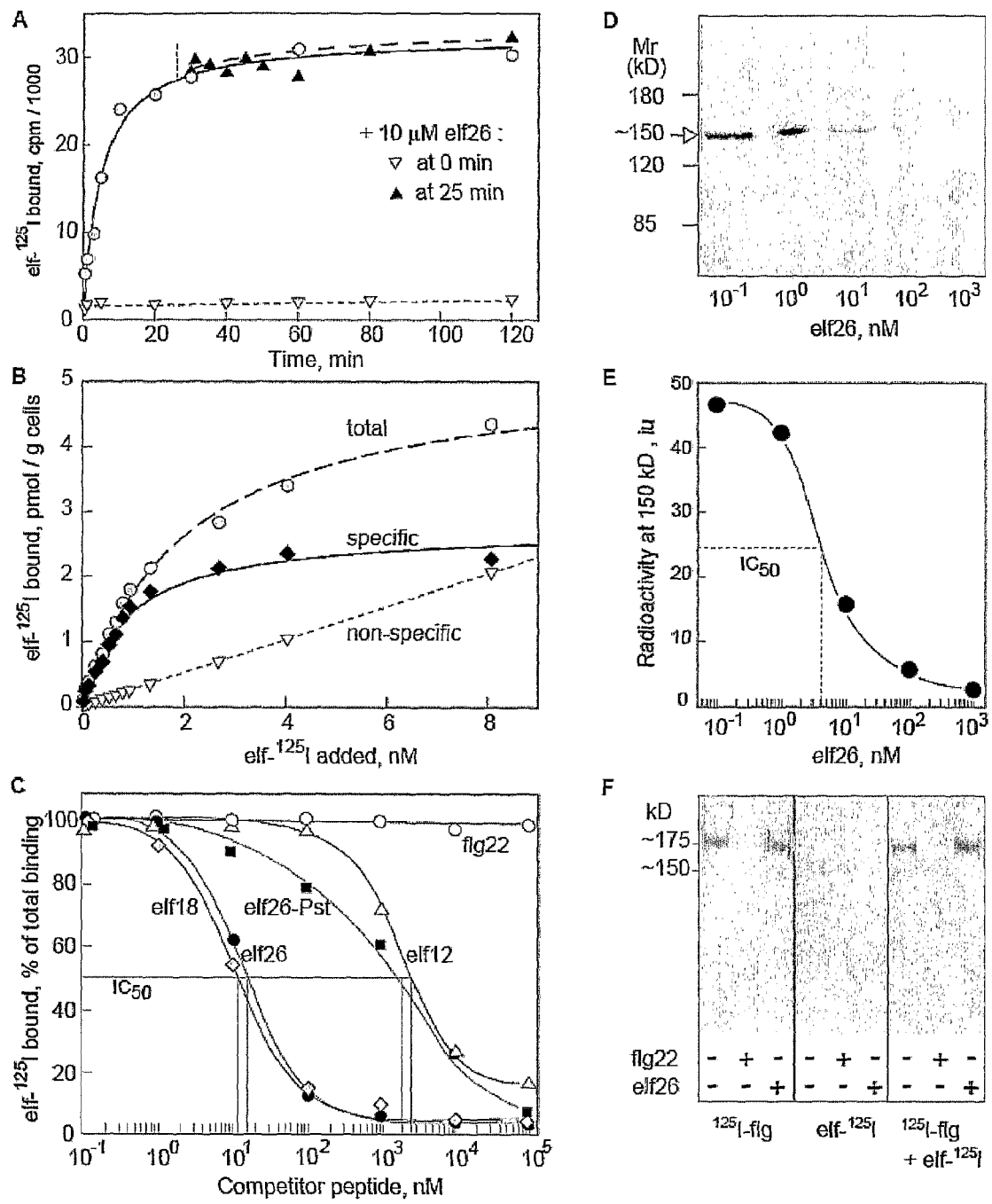
FIG. 1. Intact *Arabidopsis* cells have high-affinity binding sites specific for EF-Tu.
Figure 1G:
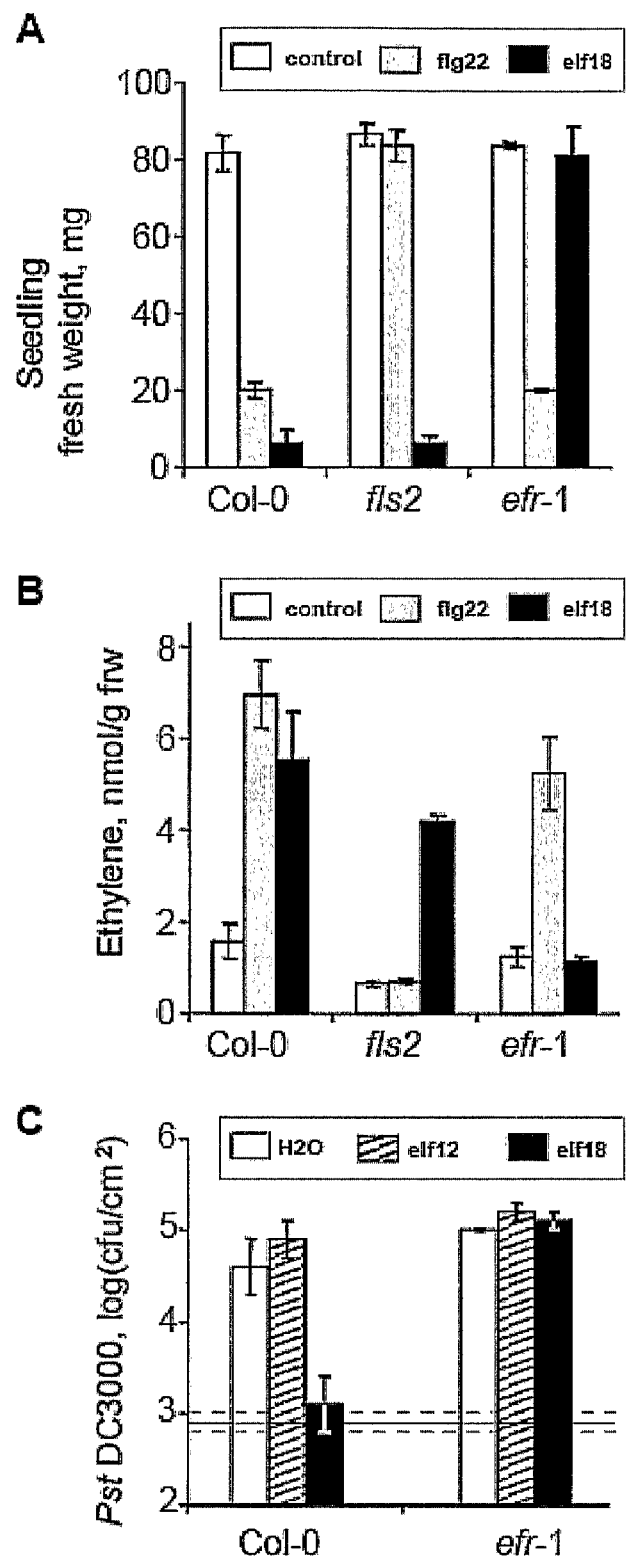

FIG. 1G. The efr-1 mutant is insensitive to elf18.

(A) Effect of elf18 and flg22 on seedling growth in wild-type Col-0, efr-1 and fls2. Five-day-old seedlings were treated with liquid MS medium alone, or supplemented with 1 µM elf18 or flg22 as indicated. Fresh weight of seedlings was determined 7 days later. Values represent average and standard variation of n=6.

(B) Ethylene biosynthesis in leaf tissues of wild-type Col-0, efr-1 and fls2 plants treated for 3 h with 1 µM elf18 or flg22 as indicated. Values represent average and standard variation of n=6 replicates.

(C) Elf18-induced resistance in wild-type Col-0 and efr-1 plants. Plants were pretreated for 24 h by leaf infiltration with water, 1 µM elf12, or 1 µM elf18. Subsequently, leaves were infected with $10^5$ cfu/ml Pst DC3000. Values represent bacteria (cfu) extractable from leaves immediately after infection (indicated by the solid and the dashed horizontal lines) and 2 days post infection as average and standard variation of n=8 replicates.

Figure 2:
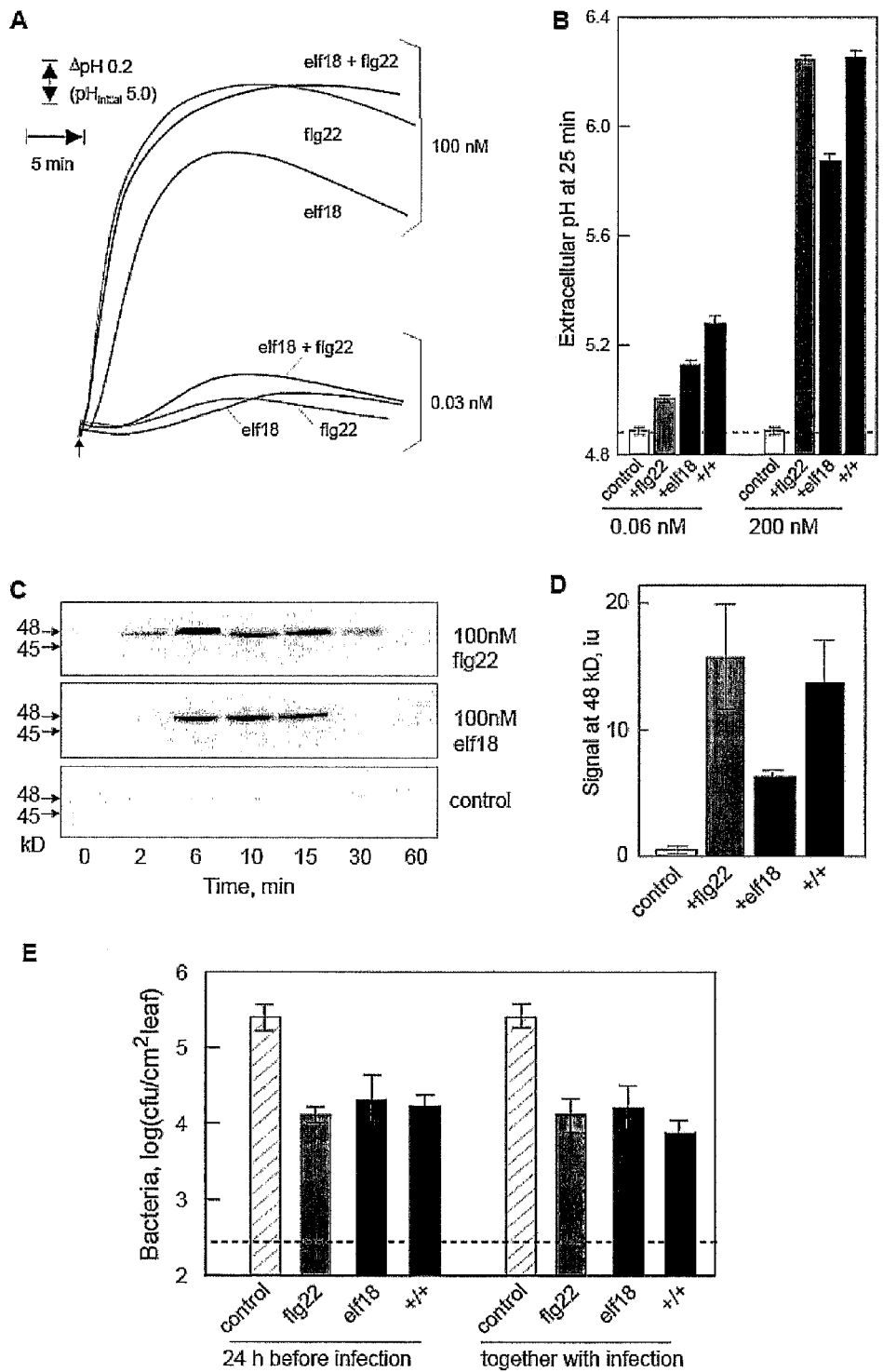

FIG. 2. Medium alkalinization, MBP kinase activities and induction of resistance after treatment with EF-Tu and flagellin.

(A) Extracellular pH in cells treated with 0.03 nM or 100 nM of flg22 or elf18 as indicated.

(B) Extracellular pH in cells treated for 25 min with flg22, elf18 or both peptides as indicated. Bars and error bars show means and standard deviations of n=4 replicates, dashed line the extracellular pH at the beginning of the experiment.

(C) Time course of MBP kinase activity in cells treated with 100 nM flg22, 100 nM elf18, or without peptide as a control. Arrows mark bands with kinase activity migrating at 48 kD and 45 kD. Gels were loaded with equal amounts of protein and the parts of the gels not shown contained no radioactively labelled bands.

(D) MBP kinase activity after 10 min of treatment with 100 nM elf18, 100 nM flg22 or a combination of both peptides. Bars and error bars indicate means and standard deviations of the integrated values for the 48 kD band from extracts of n=3 replicate treatments. Linearity of the assay was verified by loading gels with double amounts of extracts (data not shown).

(E) EF-Tu and flagellin limits growth of Pseudomonas syringae pv tomato (Pst) DC3000 in Arabidopsis. Leaves of Arabidopsis plants, 5 weeks old, were pressure infiltrated with 100 nM flg22, 100 nM elf26, or with both peptides either 24 h before or concomitantly with the Pst DC3000 bacteria ($10^5$ cfu/ml) as indicated. Bacterial growth was assessed 4 days post-infection (4 dpi). Results show average and standard error of values obtained from three plants with two leaves analyzed each (n=6). The dashed horizontal line indicates cfu extractable from leaves 1 h after inoculation (0 dpi).

Figure 3:
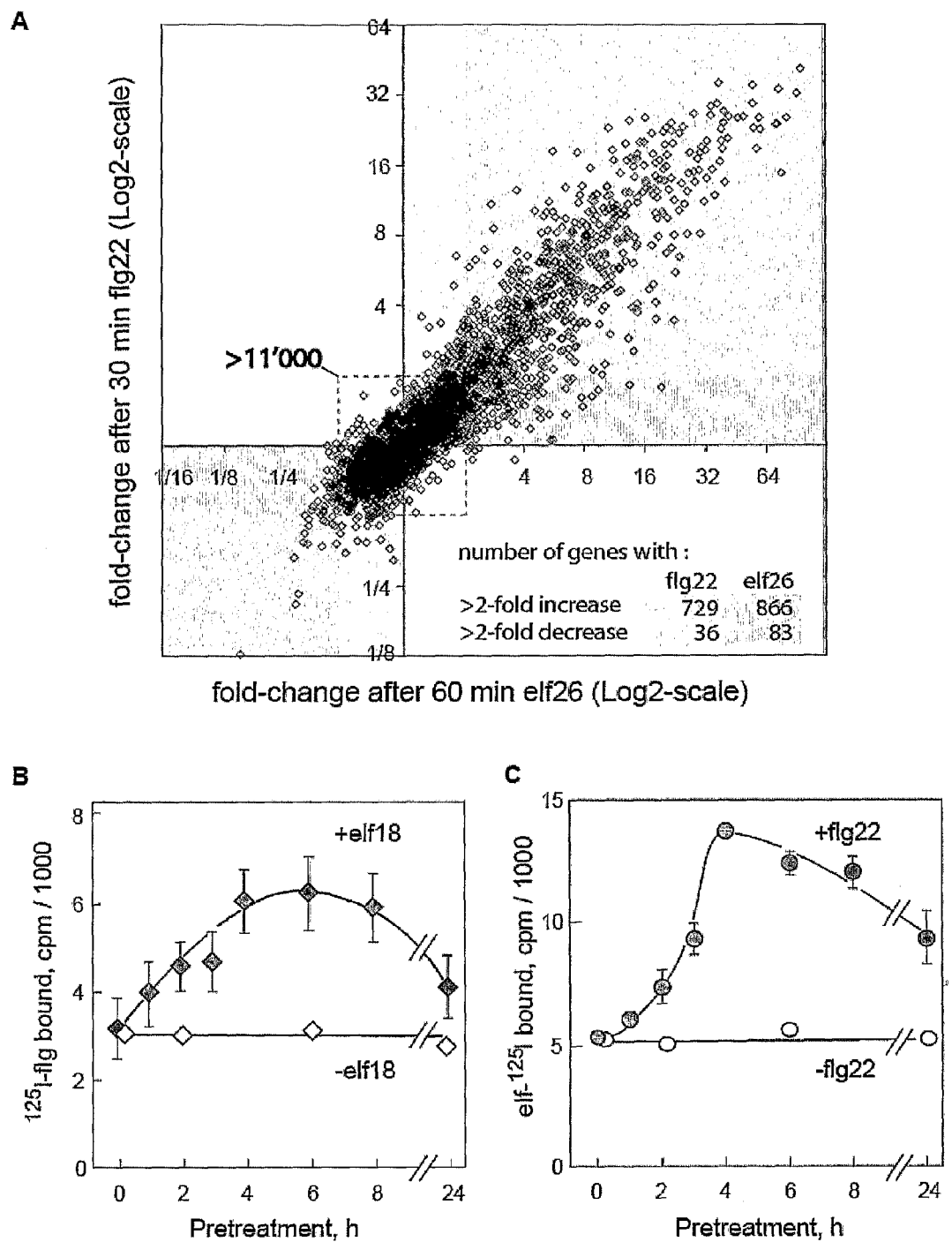

FIG. 3. Changes in transcriptome and in number of receptor binding sites in plants treated with flagellin and EF-Tu.

(A) Affymetrix ATH1 Gene array experiments with Arabidopsis seedlings treated with flg22 and elf26. Comparison of changes after treatment with elf26 for 60 min (x-axis) with those previously described for flg22 after 30 min (y-axis, values from Zipfel et al., 2004). Fold-induction (log base 2) over control levels were calculated for the 12'000 genes with significant expression in control seedlings. Most, >90% of them, show changes below 2-fold and group close to the origin of the axis (shaded in gray).

(B) Number of receptor sites for flagellin after pre-treatment of plants with elf18. Binding activity for $^{125}$I-flg in crude plant extracts of Col-0 seedlings after mock treatment (−elf18) or treatment with 1 µM elf18 (+elf18) for different times. Values show specific binding determined by subtraction of non-specific binding from total binding. Non-specific binding, radiolabel bound in the presence of 10 µM non-labelled flg22, was at ~800+/−50 cpm in all samples. Symbols and bars represent mean and standard deviation of n=3 replicate measurements.

(C) Number of receptor sites for EF-Tu after pre-treatment of plants with flg22. Binding activity for elf-$^{125}$I in crude plant extracts of seedlings after mock treatment (−flg22) or treatment with 1 µM flg22 (+flg22) for different times. Non-specific binding was at ~3000 cpm in all samples. Symbols and bars represent mean and standard deviation of n=3 replicate plant extracts.

FIG. 4. The mutant efr-1 is insensitive to elf18.

(A) Effect of elf18 on seedlings from wild-type Col-0, efr-1 (SALK_044334) and fls2. Five-day-old seedlings were treated with liquid MS medium alone (left panel), or supplemented with 1 µM elf18 peptide (right panel). Pictures were taken after one week of treatment.

(B) Oxidative burst in leaf tissues of wild-type Col-0, efr-1 and fls2 plants. Luminescence of leaf slices in a solution with peroxidase and luminol was measured after addition of 1 µM elf18 (left panel) or 1 µM flg22 (right panel). Results are averages±standard errors (n=8).

(C) Binding sites specific for EF-Tu are absent in efr-1 plants. Binding activity of wild-type Col-0 and efr-1 plant extracts was tested by adding elf-$^{125}$I alone (total binding) or with 10 µM unlabeled elf26 as competitor (non-specific binding). Symbols and bars indicate values and means of 2 replicate measurements.

(D) Chemical crosslinking with elf-$^{125}$I and plant extracts from wild-type Col-0 and efr-1 plants. Aliquots of plant extracts were incubated with elf-$^{125}$I alone or together with an excess of 10 µM of unlabeled elf18 and crosslinked by the addition of EGS. Radiolabeled proteins were analyzed after separation by SDS-PAGE with a Phosphorimager.

FIG. 5. EFR encodes a LRR receptor kinase.

(A) Schematic representation of the EFR gene. Exons are represented as black boxes with the sites of T-DNA insertions in the efr-1 and efr-2 mutants indicated by open triangles.

(B) Primary structure of the EFR protein (SEQ ID NO: 1). The amino-acid sequence predicted from the DNA sequence of EFR is shown divided into the predicted signal peptide; the N-terminal domain containing paired cysteines, indicated by black boxes and a line connecting them; the LRR domain with residues identical to the consensus sequence (SEQ ID NO: 2) marked in black; the extracellular juxta-membrane domain containing paired cysteines, indicated by black boxes and a line connecting them; the transmembrane domain with hydrophobic residues (shaded) flanked by charged, basic residues (marked in black); the intracellular juxta-membrane domain with the putative endocytosis motif YXXø (underlined); the Serine/Threonine kinase domain; the C-terminal tail.

Figure 6:
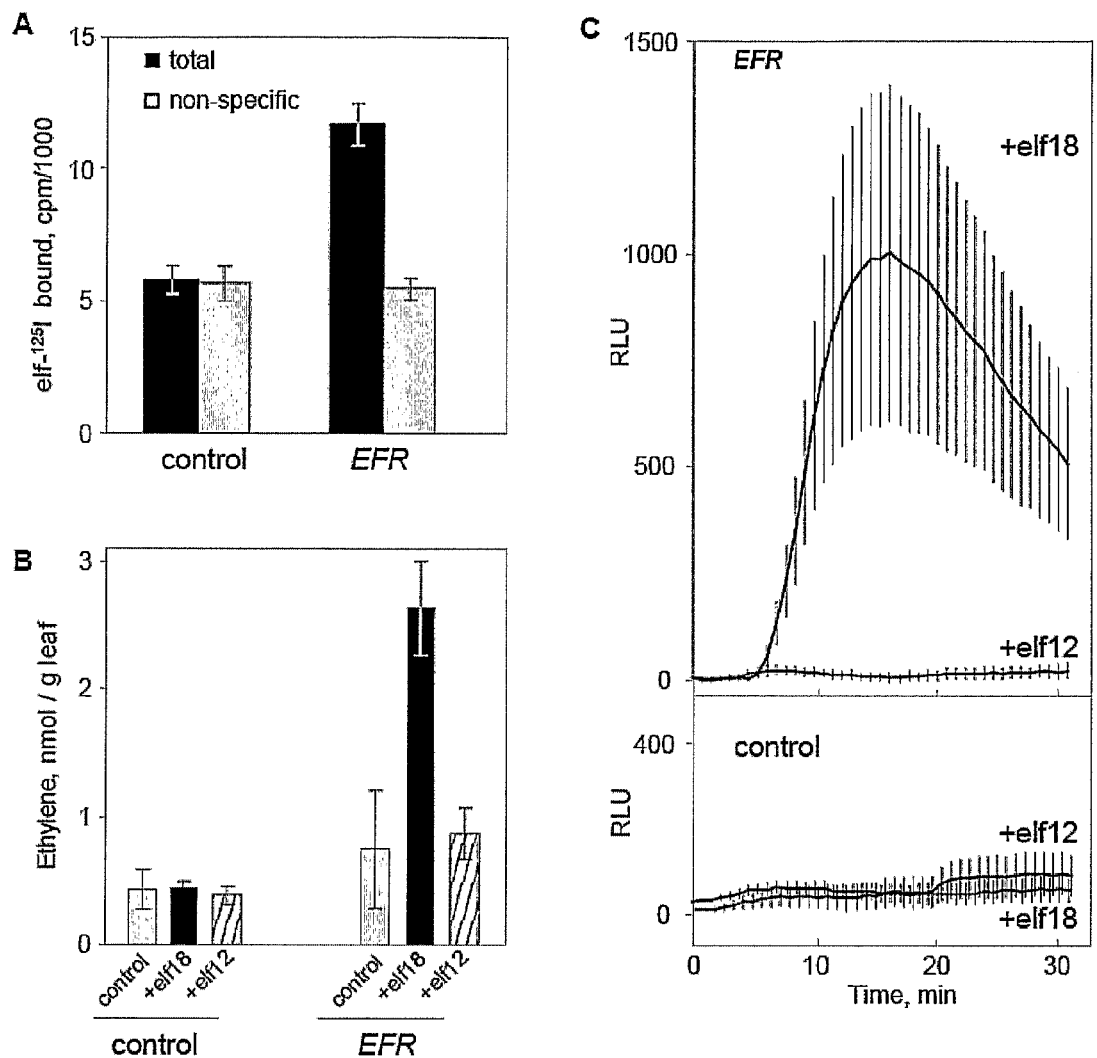

FIG. 6. N. benthamiana plants transformed with EFR show responsiveness to EF-Tu.

(A) N. benthamiana leaves transiently transformed with plasmids encoding EFR or FLS2 (control) in the T-DNA were tested for the presence of binding sites specific for EF-Tu. Binding activity in extracts was tested by adding the radiolabeled elf-$^{125}$I alone (total binding) or with 10 µM unlabeled elf26 as competitor (non-specific binding). Results are averages±standard deviations of n=4 replicate measurements.

(B) Induction of ethylene biosynthesis in leaf of N. benthamiana plants transiently transformed with EFR or AtFLS2 (control). Leaf pieces were treated with 10 µM elf18 or 10 µM of the inactive analogue elf12 as indicated. Results of ethylene accumulating over 3 h of treatment are averages±standard deviations (n=3).

(C) Oxidative burst in leaf tissues of N. benthamiana plants transiently transformed with EFR or AtFLS2 (control). Luminescence of leaf slices in a solution with peroxidase and luminol was measured after addition of 100 nM el18 or its inactive analogue elf12. Results are averages±standard error (n=6).

FIG. 7. The efr-1 mutant is more susceptible to infection and transformation by Agrobacterium tumefaciens (A) Staining for GUS activity in leaves of wild type and efr-1 after infiltration with 2*108 A. tumefaciens carrying pBIN19-35S::GUS.

(B) Quantitative GUS assays with extracts from leaves of wild type and efr-1 mutants 4 days after infiltration with 2*10$^8$ A. tumefaciens carrying pBIN19-35S::GUS. Leaves were injected with bacterial suspensions supplemented, or not, with 1 µM flg22 or elf18 as indicated. Bars and error bars represent mean and standard error of n=6 independent extractions from two leaves each.

(C) Symptoms of wild type and efr-1 leaves 7 days after pressure infiltration with 2*10$^8$ A. tumefaciens.

Figure 8:
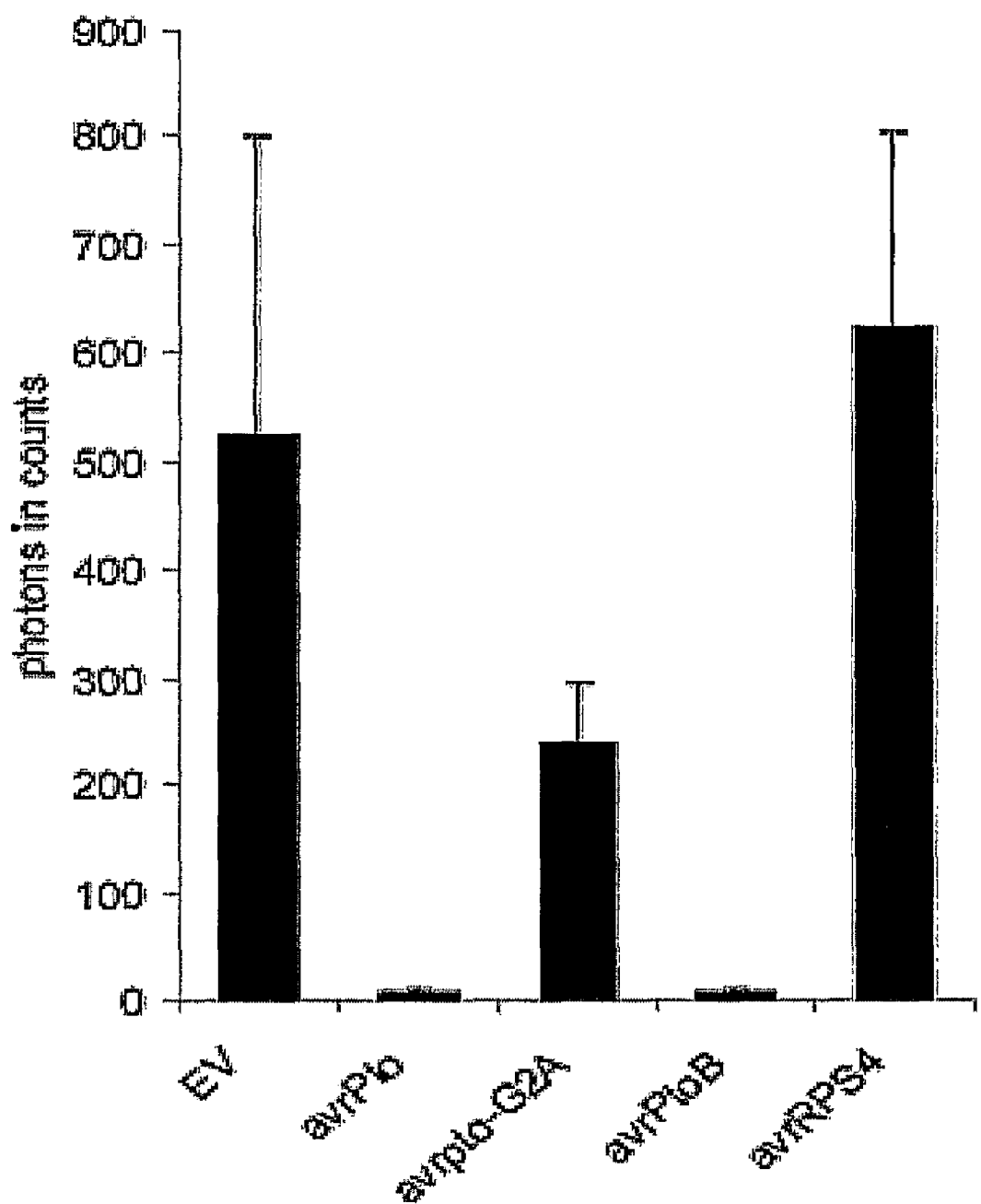

FIG. 8. Suppression of PtabF-induced ROS by AvrPto and AvrPtoB in N. benthamiana; AvrPto-G2A is a defective mutant of AvrPto. AvrPto and AvrPtoB are unrelated; Photon counts indicates the increase in ROS (the higher the more ROS is produced); represents 6 independent experiments, averaged at t=600s; leaf tissue transiently expressing the P. syringae effector proteins AvrPto, AvrPtoB and AvrRPS4; PtabF induced. Similar pattern For PtomF, flg22 & CSP22; AvrPto and AvrPtoB also suppress calcium burst in a similar fashion.

Figure 9:
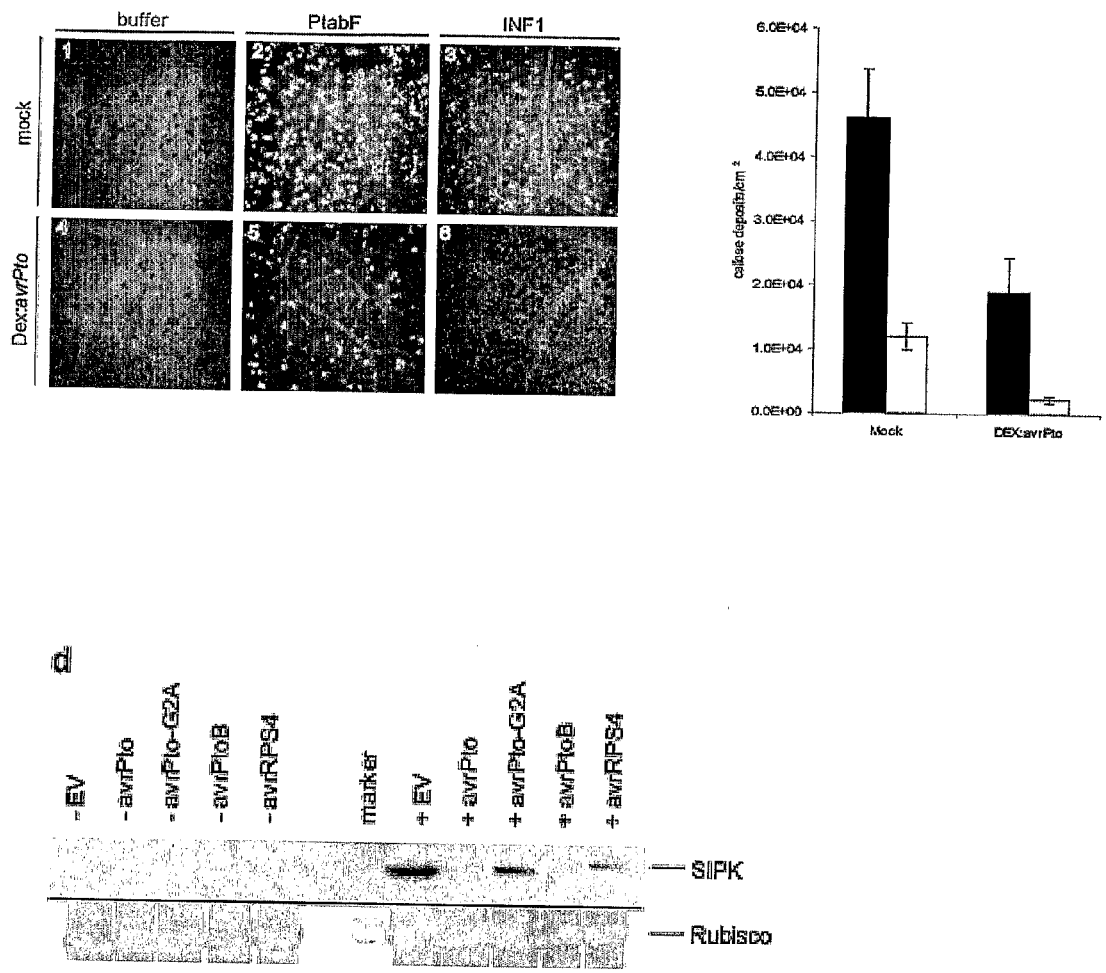

FIG. 9. Suppression of callose-deposition and MAPK activation by AvrPto & AvrPtoB; All in N. benthamiana; Top left: Suppression of callose deposition (light spots) by avrPto (stable transgenic N. benthamiana). Top right panel: quantitation of callose deposits (black: induced with flagellin & white induced with INF1); lower part: Western Blot to detect activated SIPK (a MAP Kinase from N. benthamiana). Left is the negative control where water was used for the elicitation & right (+) flagellin used for the elicitation; Anti-pERK1-2 Western blot for detection of MAPK activation; −=uninduced; +=induced with PtabF; −>similarly for INF1, CSP22, PtomF & flg22.

FIG. 10. Nonhost HR induced by flagellin; Flagellin from Pseudomonas syringae induces a so-called nonhost HR on Solanaceous species; No flagellin HR in Arabidopsis; Flagellin was also found to induce the HR in rice; Flagellin from Pseudomonas syringae induces a nonhost HR on Solanaceous species—here: 76R=tomato & N.b. =N. benthamiana. A gel on the flagellin purification demonstrated that the sample was highly pure (mass spec & silver staining).

Figure 11:
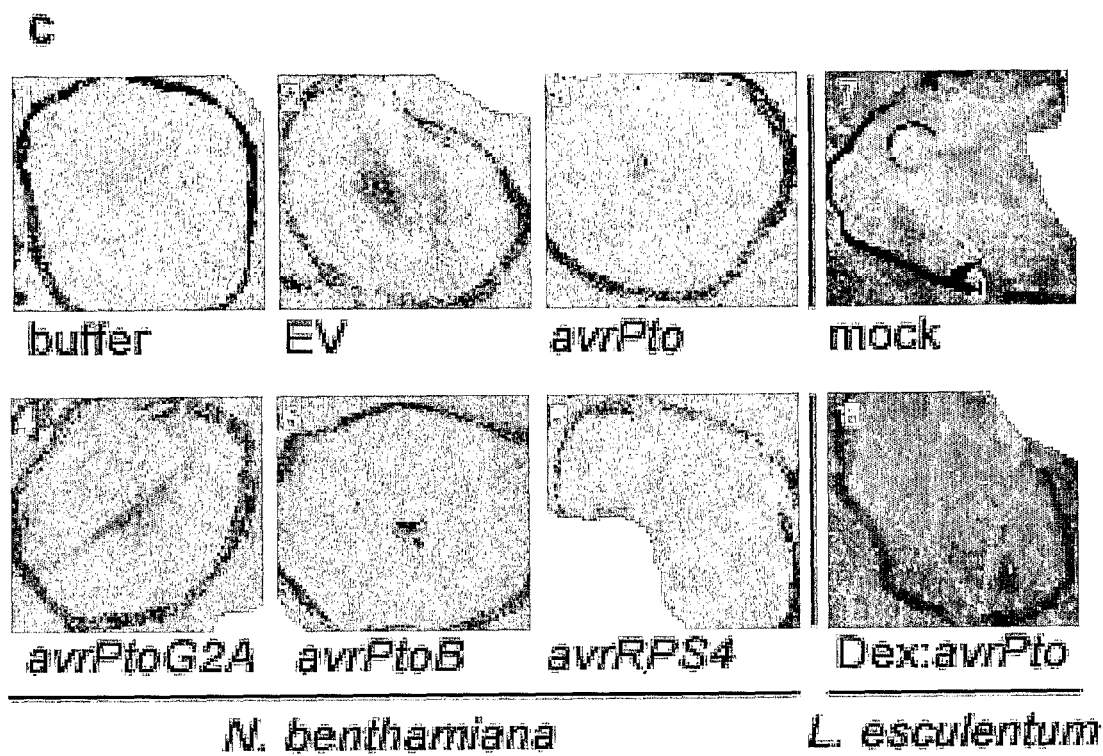

FIG. 11. AvrPto and AvrPtoB suppress the HR induced by flagellin; AvrPto & AvrPtoB suppress this nonhost HR in tomato & N. benthamiana; Similar results with INF1

Figure 12:
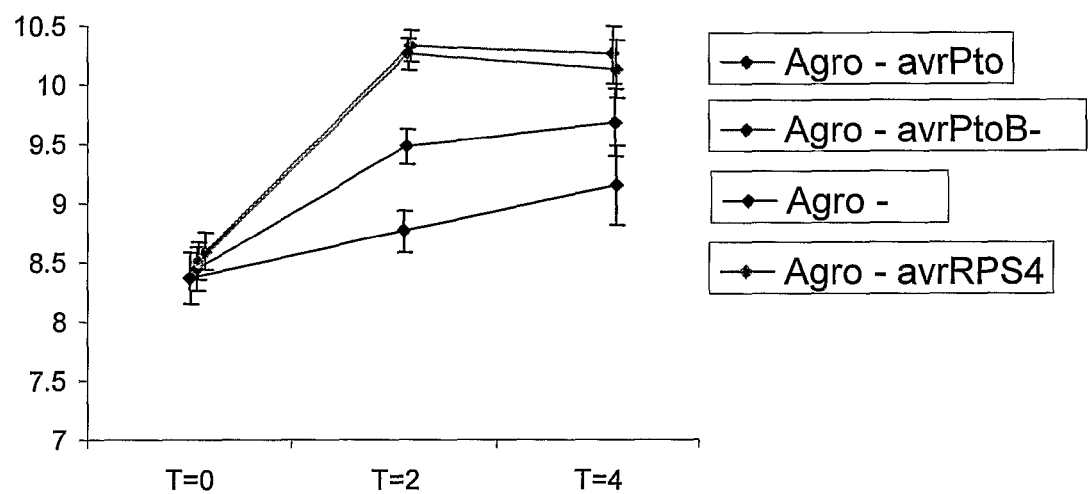

FIG. 12. AvrPto and AvrPtoB act as pathogenicity factors and allow A. tumefaciens to grow on N. benthamiana. AvrPto & AvrPtoB can enhance the growth of Agrobacterium (C58C1) when transiently expressed (by the same Agro strain) in N. benthamiana. This means that there is a PAMP other than EF-Tu (which is not recognized in N. benthamiana), that restricts growth of Agrobacterium in N. benthamiana. Y axis=log cfu/square cm.

Figure 13:
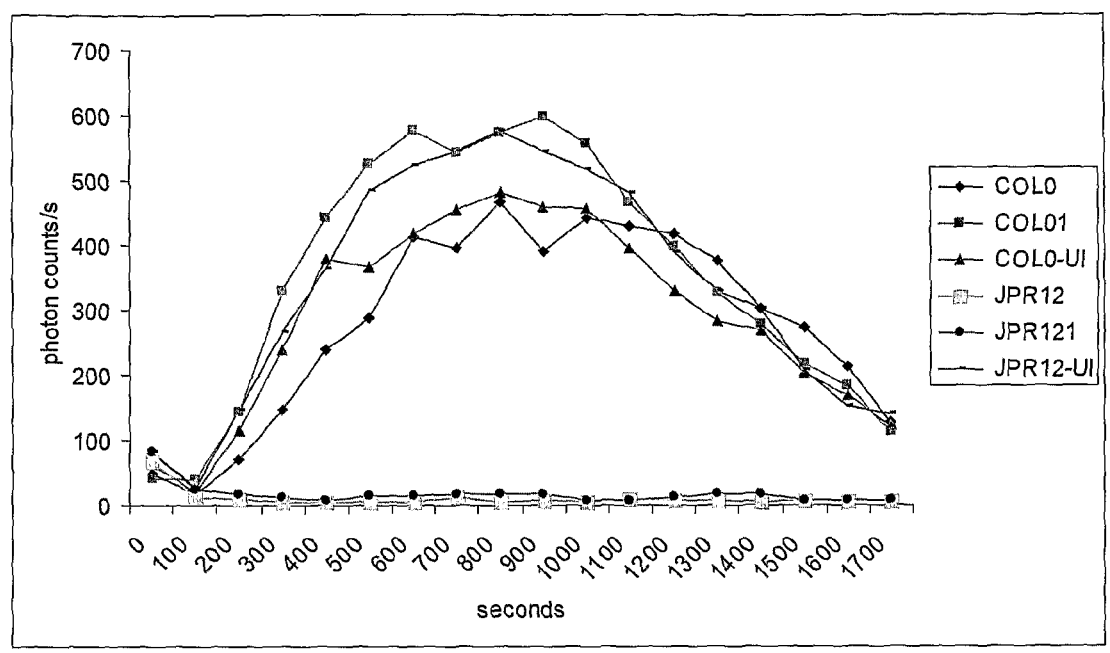

FIG. 13. Suppression of oxidative burst in Arabidopsis by AvrPto; The exact same result was achieved with AvrPtoB. Western Blot confirms the expression of the protein. The fluorescence provided a visual readout of the ROS meassurement (light blue circles showed the accumulation of ROS in the periphery of a leaf disc). The excel graph is a quantitative readout of the same experiment.

Figure 14:
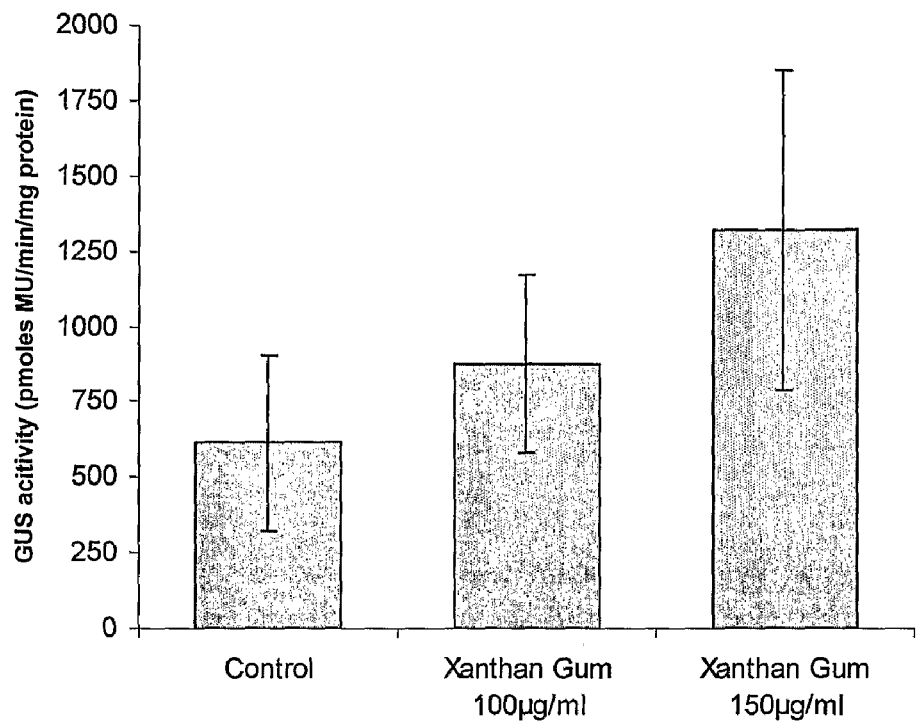

FIG. 14. Quantification of GUS expression in leaves after co-infiltration with high concentrations of xanthan gum and Agrobacterium carrying GUS-HA (hemagglutinin).

Figure 15:
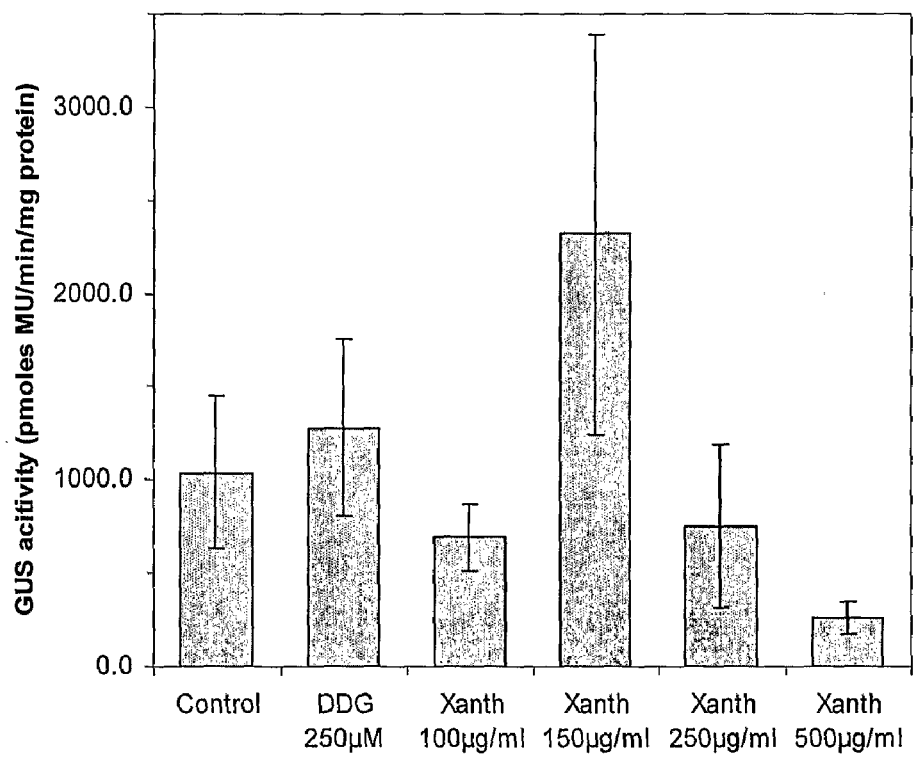

FIG. 15. Quantification of GUS expression in leaves pretreated with various concentrations of xanthan gum or 2-DDG.

Figure 16:
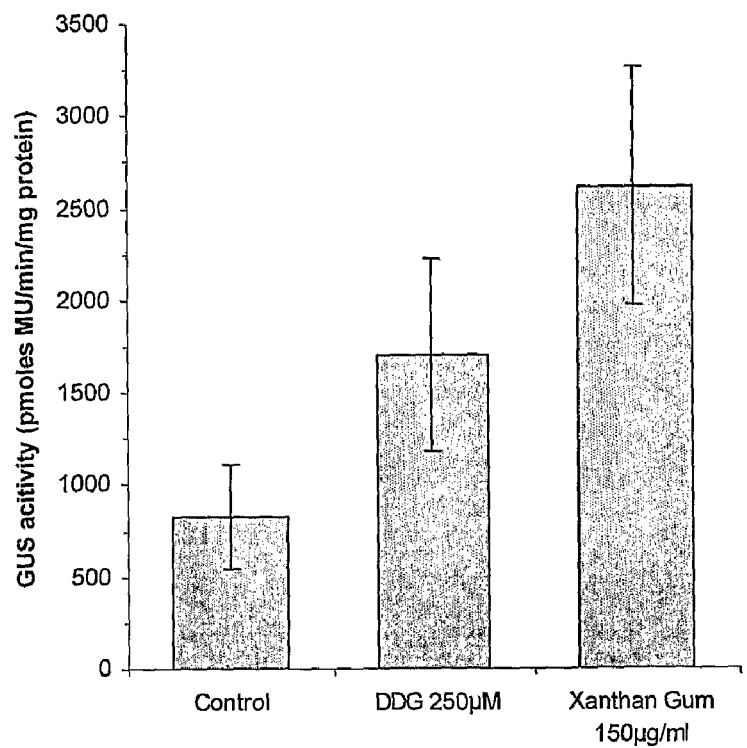

FIG. 16. Quantification of GUS expression in leaves sprayed one day prior to Agrobacterium infiltration with xanthan gum or 2-DDG.

Figure 17:
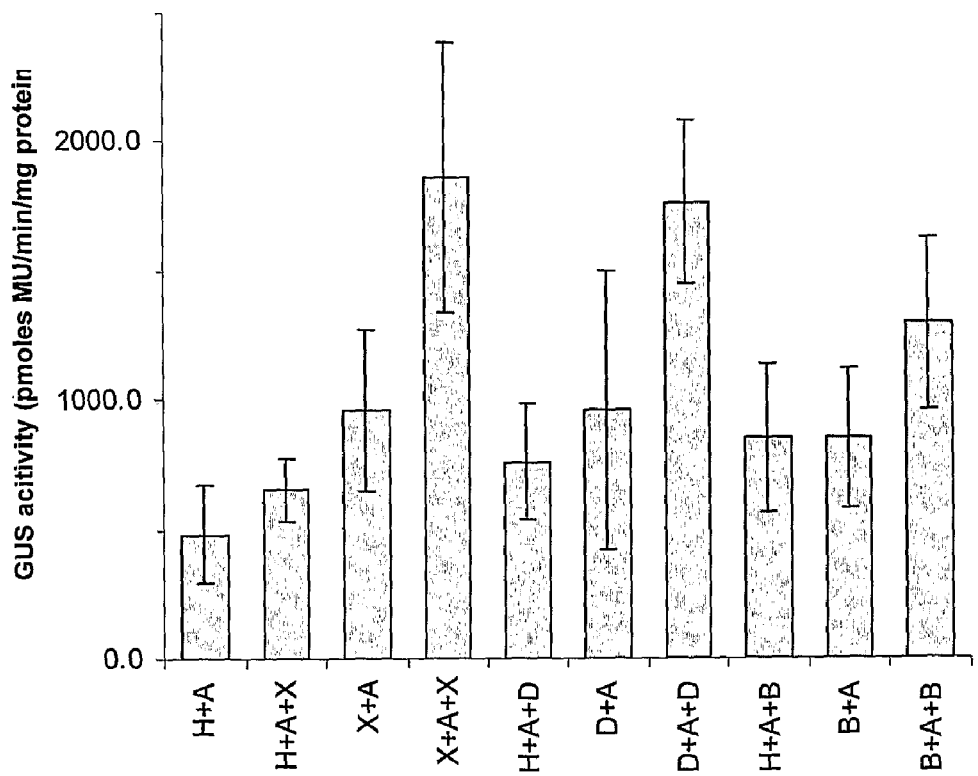

FIG. 17. Quantification of GUS expression following pre-spray or co-infiltration of xanthan gum or/and 2—DDG. Legend: H—Water; A—Agrobacterium; X—Xanthan gum 150 µg/ml; D—2-DDG 250 µM; B— Xanthan gum 150 µg/ml+ 2-DDG 250 µM; Letter before A means pretreatment with respective chemical spray or water spray; Letter after A means chemical mixed with the Agrobacterium inoculum.

SUMMARY OF THE INVENTION

Higher eukaryotes sense microbes through perception of pathogen-associated molecular patterns (PAMPs). The flagellin receptor FLS2 represents so far the only known pattern recognition receptor (PRR) in Arabidopsis. Arabidopsis plants detect a variety of PAMPs including specific epitopes of the bacterial proteins flagellin and EF-Tu. Here, we show that flagellin and EF-Tu activate a common set of signalling events and defence responses, but without clear additive or synergistic effects. Treatment with either PAMP results in increased receptor sites for both PAMPs, a finding employed in a reverse-genetic approach to identify the receptor kinase EFR as the EF-Tu receptor. Transient expression of EFR in *Nicotiana benthamiana* results in formation of specific binding sites for EF-Tu, and responsiveness to this PAMP. *Arabidopsis* efr mutants show a higher frequency of T-DNA transformation by the bacterium *Agrobacterium tumefaciens*, revealing a role for EF-Tu perception in restricting this plant pathogen. These results demonstrate that EFR is the receptor for EF-Tu and that plant defence responses induced by PAMPs like EF-Tu reduce transformation by *Agrobacterium*.

Accordingly, those skilled in the art will appreciate that this invention comprises at least the following embodiments relating to methods by which the defence response to *Agrobacterium* can be reduced, resulting in elevated transformation frequency, and applications of that elevated transformation frequency:

(a) A method for stable transformation of plants with genes that compromise resistance, creating plant genotypes in which plant defences to *Agrobacterium* are reduced;
(b) A method for transient transformation of plants with a mixed inoculation of *Agrobacterium* carrying genes that compromise resistance;
(c) A method for deployment of chemicals including, but not limited to, small molecule effectors and peptides that suppress the plant defence response;
(d) A method for genetic modification of *Agrobacterium* with systems to suppress or reduce host defence, and the thus modified *Agrobacterium*.
(e) A method for application of elevated transformation frequency to homology-dependent gene targeting using co-delivery with 35S:RAD54.

Other objects, embodiments and advantages of this invention will be appreciated from a review of the complete disclosure and the claims appended hereto.

Where the claims discuss a method for enhancing the plant transformation efficiency of a bacterium, it will be understood that the invention likewise provides a method for enhancing the transformation efficiency of a plant by a bacterium which comprises modifying a plant as per a method set out in the present specification (including claims) and optionally contacting it with the bacterium (e.g. containing a gene of interest) to thereby transform the plant. As described below, the modification of plant may involve reducing the activity of a PRR in the plant or an ancestor thereof. The contacting will preferably be subsequent to the modification of the plant.

It will likewise be understood that where the claims discuss a method for enhancing the plant transformation efficiency of a bacterium, it will be understood that the invention likewise provides a method for enhancing the transformation efficiency of a plant by a bacterium (e.g. containing a gene of interest) which comprises modifying the bacterium as per a method set out in the present specification (including claims) and optionally contacting it with the plant to thereby transform the plant.

DETAILED DESCRIPTION OF THE PREFERRED EMBODIMENTS OF THE INVENTION

Many years of research have focused on different aspects of the *Agrobacterium tumefaciens*-host interaction, such as cell-cell recognition and cell-to-cell transport, nuclear import, assembly and disassembly of protein-DNA complexes, DNA recombination, and regulation of gene expression (Gelvin, 2003; Tzfira et al., 2004). However, the extent to which *Agrobacterium* is initially recognized as a pathogen and the potential effect of plant defence responses on transformation efficiency have received little attention.

Plants can perceive bacteria by perceiving conserved molecules from the bacteria, referred to as pathogen-associated molecular patterns (PAMPs) (Nurnberger et al., 2004), such as flagellin or EF-Tu (Felix et al., 1999; Kunze. G et al., 2004). PAMPs are recognized through pattern recognition receptors (PRRs) that are often transmembrane receptor kinases with extracellular leucine-rich repeats (Zipfel and Felix, 2005). Activation of these receptors by elicitors results in defence activation including production of reactive oxygen species, callose synthesis and other cell wall changes, activation of mitogen-activated protein (MAP) kinase signalling, and induction of a plethora of genes that directly or indirectly contribute to defence (Navarro et al., 2004; Nurnberger et al., 2004; Zipfel et al., 2004).

We have recently identified the *Arabidopsis* EF-Tu receptor as the receptor kinase EFR (At5g20480). Interestingly, we found that *Agrobacterium*-mediated transient expression in efr mutant plants was on average ~14-fold higher than in wild-type, revealing that EF-Tu perception by the plant restricts transformation by *Agrobacterium*. Reciprocally, we found that addition of active EF-Tu- or flagellin-derived peptides to the *Agrobacterium* inoculum almost completely suppresses plant transformation. Although the flagellin peptide recognized by most plants (flg22) derived from *A. tumefaciens* is inactive as an inducer of plant defences, we found that *Arabidopsis* mutated for the flagellin receptor, FLS2, are nevertheless more amenable to *Agrobacterium*-mediated transient expression. A combination of the efr and fls2 mutations gives an even better expression than in individual mutants. In addition, the *Arabidopsis* ecotype Ws-0, which is a natural fls2 mutant (Zipfel et al., 2004), is one of the best ecotypes for high level transient expression in *Arabidopsis* (our observations & Wroblewski et al., 2005). These observations suggest that flagellin perception by FLS2 also plays a role in *Agrobacterium* recognition. Without wishing to be bound by mechanistic considerations, this may be explained by the fact that FLS2 recognizes a flg22 sequence derived from one of the three other reported flagellin genes present in *Agrobacterium* (Deakin et al., 1999) and/or that FLS2 recognizes an additional sequence other than the flg22 epitope.

There are at least four steps at which plant defence processes could interfere with the *Agrobacterium*-mediated transformation process: (1) bacterial attachment to the plant cell surface; (2) transfer of the T-DNA into the plant cell and then (3) into the nucleus, and, finally, (4) stable integration of T-DNA into the plant genome (Gelvin, 2003). The transient expression assay used in our study does not necessarily involve this last step of stable integration of the T-DNA into the plant genome. However, since our results indicate that at least one of the earlier steps is blocked by the plant innate immune system, we anticipate that this defence response will also affect the frequency of stable transformation.

Many different elicitors from diverse pathogens elicit defence responses in plants. These are believed to activate PAMP receptors on the surface of plant cells. We and others (see references below) have shown that some type-III effector proteins of phytopathogenic bacteria, which are secreted directly into the plant cell, are capable of suppressing plant defence responses (Espinosa and Alfano, 2004; Kim et al., 2005; Nomura et al., 2005). Notably, our work has shown that type-III effectors e.g. AvrPto and AvrPtoB inhibit defence responses in a broad-spectrum and non-specific manner. These results have important biotechnological implications because expression of one of these effectors is sufficient to abrogate the defence response in the absence of precise knowledge of the elicitation event. In addition, we have shown that expression of one such effector enhances the growth of Agrobacterium in planta. Thus, the defence response to Agrobacterium has been inhibited by the effector protein, which is likely to enhance the subsequent transformation frequency.

These results clearly demonstrate that perception of Agrobacterium by the plant defence system restricts its ability to transform plant cells. Interestingly, recent studies show that Agrobacterium induces plant defence gene expression (Ditt et al., 2005; Ditt et al., 2001; Veena et al., 2003). In addition, the Arabidopsis cep1 mutant that constitutively expresses defence-related genes is more resistant to Agrobacterium infection (Zhu et al., 2003). Finally, the Agrobacterium catalase KatA gene is required for its full virulence (Xu et al., 2001; Xu and Pan, 2000), and might therefore counteract the toxic effect of $H_2O_2$, one of the major components of the plant defence system.

The identity of the bacterial and plant molecule(s) involved in these responses was unknown prior to the instant patent disclosure. Our work clearly demonstrates a role for EF-Tu, but also of flagellin perception in restricting Agrobacterium infection. It is interesting to note that N. benthamiana plants, which belong to the Solanaceae, do not respond to EF-Tu (Kunze et al., 2004) and are highly sensitive to Agrobacterium infection. However, based on our research, we anticipate that Agrobacterium displays additional PAMPs that are recognized by Arabidopsis and/or other plant species. Based on the current knowledge of PAMP perception in plants we anticipate that differences in transformation efficiency observed between plant genotypes or species is explained by their different responsiveness to PAMPs. Many crop species remain difficult to transform with Agrobacterium. Therefore, our findings enable manipulation of plant defences in recalcitrant plants to allow more efficient transformation by Agrobacterium.

Methods by which the Defence Response to Agrobacterium can be Reduced, Resulting in Elevated Transformation Frequency, and Applications of that Elevated Transformation Frequency These methods can be divided into 6 main categories.

Stable Transformation of Plants with Genes that Compromise Resistance, Creating Plant Genotypes in which Plant Defences to Agrobacterium are Reduced.

In addition to the positive effect of the efr and the fls2 mutations of plant transformation, we found that additional mutants for known defence-associated genes give a similar phenotype. Most of these mutants are impaired in the salicylic-acid pathway of plant defence that is known to be important for efficient immunity to biotrophic pathogens (Glazebrook, 2005). The following mutants or transgenic lines were already found to be more susceptible to Agrobacterium-transient transformation: 35S::nahG, sid2, eds5, pad4, pad2, ndr1 and eds1.

Utilizing "tilling" (targeted induction of local lesions) (Slade and Knauf, 2005), defence mutants in any given plant species are identified. An elite varietal genotype is identified and a mutagenized population is screened for mutants in efr or fls2. In addition, a transgenic line is generated which expresses the 35S::nahG transgene (Gaffney et al., 1993). After transformation, the transgene is crossed out.

Another approach involves constitutive or inducible expression of microbial effectors by the plant. Many phytopathogenic bacteria use a type three secretion system (TTSS) to deliver effector proteins into plant cells that suppress defences elicited by PAMPs (Espinosa and Alfano, 2004; Nomura et al., 2005). In addition, it is likely that many other classes of pathogens encode similar proteins that are able to suppress defence response in plant cells. Such proteins are useful in the strategies described here.

The TTSS-delivered effector molecules are recognized by resistance (R) genes, resulting in defence activation (Dangl and Jones, 2001). Many effectors were originally discovered as so-called avirulence (Avr) genes recognized by specific R genes. However, if they are not recognized, many have been shown to suppress defence. Examples include AvrRpt2 (Chen et al., 2000), AvrRpm1 (Kim et al., 2005; Ritter and Dangl, 1995) and AvrPto (Hauck et al., 2003). We have found that expression of 35S::AvrPto or 35S::AvrPtoB in Arabidopsis or Nicotiana benthamiana suppresses plant responses to the microbial elicitors, flagellin, INF1 and CSP22. These findings provide a method to enhance Agrobacterium-mediated transformation of recalcitrant species. The important aspect of such methods is delivery of a suitable defence-suppressing effector protein such as AvrPto or AvrPtoB to the cell during the plant transformation procedure. Many different strategies for delivery of the effector proteins are possible. For example, the protein may be purified from a suitable source and delivered to plant cells or protoplasts by bombardment, membrane fusion or electroporation. Alternatively, transgenic plants may be made that express a gene encoding a bacterial effector protein under control of an inducible promoter. Induction of expression of the effector transgene prior to co-cultivation with Agrobacterium inhibits Agrobacterium-elicited defence responses. The effector transgene may be segregated away from the desired transgene after identification of transformed lines. Alternatively, the effector transgene may be expressed transiently after delivery from Agrobacterium. In this scenario, there are two separate transformation events; delivery of the effector transgene, and delivery of the transgene of interest. In one embodiment of this method, the transgenes are delivered concomitantly. Alternatively, the effector transgene is delivered before the transgene of interest, to ensure abrogation of Agrobacterium-mediated defence responses and thus enhance transformation efficiency. In the co-transformation procedure, the effector transgene may be removed by failing to select for its insertion into genomic DNA, or it may be removed after transformation by genetic segregation.

Transient Transformation of Plants with a Mixed Inoculation of Agrobacterium Carrying Genes that Compromise Resistance The same set of genes that may be introduced stably as described above (35S:nahG, 35S:avrPto 35S:avrRpm1 35S: AvrRpt2 and other effectors) may also be delivered transiently. This is achieved using mixed or sequential exposure of plant cells to Agrobacterium strains carrying a defence-suppressing effector, and strains that transform a plant variety with a gene of interest. Alternatively, two compatible binary plasmids are situated in the same Agrobacterium strain, so that transformation of T-DNAs carrying the defence-suppression gene construct and T-DNAs carrying the gene of interest occurs in parallel. Subsequently lines are selected via different antibiotic resistance in which the gene of interest has been stably delivered and in which the defence-suppressing transgene has segregated away via mendelian inheritance, provided, of course, that the T-DNA entered the genome in an unlinked position.

Discovery and Deployment of Chemicals Including Peptides that Suppress the Plant Defence Response All previous methods are based on transient or stable genetic modifications of the host. An alternative approach is to supply compounds that, when added to the *Agrobacterium* inoculum used for the transformation, inhibit or suppress plant defences.

Many natural or synthetic chemicals may be used to suppress plant defences, including but not limited to the group consisting of:

Catechol; jasmonates, such as MeJA; coronatine; mycotoxins such as Fumonisin B made by *Fusarium moniliforme*, deoxynivalenol (DON) made by *Fusarium* and *Aspergillus* species (Nelson et al., 1993); secondary products as well as proteins, such as that produced by an avirulence gene in the rice blast pathogen *Magnaporthe grisea*, which encodes a polyketide synthase (Bohnert et al., 2004); Cytochalasin E, which interferes with actin polymerisation and interfered with cell wall-based defences to powdery mildew fungus (Yun et al., 2003); and auxin (Glickmann et al., 1998; O'Donnell et al., 2003).

A screen for additional appropriate compounds is established to identify chemicals that suppress plant defences. Thus, for example, as the flagellin and EF-Tu receptors perceive peptides, peptide libraries are screened for antagonistic peptides that bind irreversibly to the receptors, but without inducing any eliciting activity. Such peptides impede further binding of the elicitor active epitope from the previously mentioned PAMPs.

In vitro systems may be designed to identify compounds capable of binding the EFR gene products. Compounds identified may be useful, for example, in methods of enhancing the efficiency of the transformation of a plant by a bacterium.

The principle of the assays used to identify compounds that bind to the EFR gene product may involve preparing a reaction mixture comprising the EFR gene product and the test compound under conditions and for a time sufficient to allow the two components to interact and bind, thus forming a complex that can be removed and/or detected in the reaction mixture. These assays may be conducted in a variety of ways. For example, one method to conduct such an assay would involve anchoring EFR gene product or the test substance onto a solid phase and detecting EFR gene product/test compound complexes anchored on the solid phase at the end of the reaction. In one embodiment of such a method, the EFR gene product may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labelled antibody specific for the previously non-immobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for EFR gene product or the test compound to anchor any complexes formed in solution, and a labeled antibody specific for the other component of the possible complex to detect anchored complexes.

Following this initial screening for binding, assays for activation (or non-activation) of the receptor in vivo can be performed as described elsewhere herein.

We have established lines in which promoters of two *Arabidopsis* genes that are rapidly and strongly induced by flagellin (AtMyb15 and AtZat12) (Navarro et al., 2004) are fused to the luciferase reporter gene. Using techniques well known to those skilled in the art, a chemical genetics screen is conducted for compounds or also for peptides that block elevation of expression of the luciferase transgene fusion by flg22.

Genetic Modification of *Agrobacterium* with Systems to Suppress or Reduce Host Defence In another embodiment of this invention, *Agrobacterium* itself is modified to create a new strain that elicits less or no plant defence responses.

According to this embodiment, an *Agrobacterium* strain that secretes TTSS-effectors derived from pathogenic bacteria is constructed. However, as *Agrobacterium* does not possess any TTSS (Preston et al., 2005) a functional TTSS is integrated into *Agrobacterium*. This is achieved by transforming *Agrobacterium* with the pHIR11 hopPsyA cosmid that contains all TTSS genes from Pst DC3000 required for a functional system. This approach has been successfully employed to transfer this TTSS to *P. fluorescens* or *E. coli* (Collmer et al., 2000; Huang et al., 1988). Thus, TTSS competent *A. tumefaciens*, is used to express the effectors mentioned previously to suppress plant defences. Such an *Agrobacterium* strain contains four different plasmids that have to be compatible: the Ti plasmid, the pHIR11hopPsyA cosmid expressing the TTSS, a plasmid expressing an effector with its TTSS signal, and finally the binary vector containing the transgene of interest.

In a further embodiment, the capacity to transfer a T-DNA is conferred on a bacterial strain already possessing a functional TTSS, such as Pst DC3000. *Rhizobium* bacteria expressing a Ti plasmid from *A. tumefaciens* have been recently shown to be able to transform plant cells (Broothaerts et al., 2005).

In a further embodiment, *Agrobacteria* are co-inoculated with other bacteria (including *Agrobacteria* engineered as above, but lacking the T-DNA) that suppress host defence in sequential and/or mixed infections.

Application of Elevated Transformation Frequency to Homology-Dependent Gene Targeting Using Co-Delivery with 35S:RAD54

Gene targeting is still difficult in plants and cannot be used as a routine technique for gene replacement. A recent published report (Shaked et al., 2005) showed that gene targeting efficiency could be enhanced in *Arabidopsis* plants expressing the yeast RAD54 gene. The transformation efficiency in this transgenic background even further increases the rate of homologous recombination. This is achieved by crossing plant defence mutants, such as the double fls2 efr mutant, with the RAD54 line, and testing for gene targeting efficiency. This co-delivery of 35S::RAD54 T-DNA, and T-DNA carrying a gene of interest in a mixed inoculation, results in elevated homologous gene targeting frequencies in any plant amenable to transformation by *Agrobacterium*.

EFR is the *Arabidopsis* Receptor for EF-Tu

In this patent disclosure we report the identification of EFR as the EF-Tu receptor in *Arabidopsis*. This identification is based on genetic evidence that demonstrates the importance of the EFR gene in EF-Tu perception with loss of function in *Arabidopsis* mutants defective in EFR and gain of function in *N. bethamiana* plants transgenic for the *Arabidopsis* EFR gene. Furthermore, the presence of a specific, high-affinity binding site for EF-Tu detectable by biochemical binding assays and chemical crosslinking correlates with the presence of an intact EFR gene in *Arabidopsis* and *N. bethamiana*, thus demonstrating that EFR is the receptor site for EF-Tu. Perception of EF-Tu and flagellin exhibit many common characteristics of ligand-receptor interaction, receptor activation and response induction. Consistent with these features, the EF-Tu receptor EFR and the flagellin receptor FLS2 are closely related receptor kinases with LRR-ectodomains belonging to the same subfamily LRR-XII of *Arabidopsis* RLKs (Shiu and Bleecker, 2001a). Thus, besides FLS2, EFR constitutes a second example for a RLK acting as a PRR in *Arabidopsis*. Although numerous other molecular patterns characteristic for bacteria, fungi or oomycetes have been reported to act as PAMPs in plants (NOrnberger et al., 2004) the corresponding PRRs have been reported for only two of them. The first of these examples is the 75 kDa glucan-binding protein (GBP) that constitutes the high-affinity binding site for *Phytophtora* β-glucan in soybean (Umemoto et al., 1997). GBP is a soluble, extracellular protein with an intrinsic β-1,3-glucanase activity (Fliegmann et al., 2004) that seems to require a yet unknown receptor component for transmembrane signalling and formation of a functional receptor complex (Fliegmann et al., 2004). The second, more recent example refers to the receptor binding sites for the fungal elicitor EIX (ethylene-inducing xylanase) in tomato (Ron and Avni, 2004). These binding sites are encoded by the two highly related genes LeEIX1 and LeEIX2 and contain LRR ectodomains and transmembrane domains but no intracellular kinase domains. As such, they belong to the family of receptor-like proteins (RLP). Several members of the RLPs have been identified as resistance (R) genes (Nimchuk et al., 2003).

Although proteins other than RLKs and RLPs might function as PRRs as well, members of these large protein families are primary candidates for further receptors detecting additional pathogen-related molecular structures. A reverse-genetic approach, as successfully used herein helps to identify further PRRs. Thereby, receptor candidates are found in the subgroup of RLKs and RLPs found to be induced after treatment with flagellin, EF-Tu or any other PAMP. Data available in the gene expression database Genevestigator (Zimmermann et al., 2004) show that the FLS2 and EFR genes are rapidly induced also by other PAMPs like bacterial LPS, fungal chitin and the oomycete-derived NPP1 (data not shown). In turn, we can anticipate that the >100 RLKs (>15% of all RLKs) induced by bacterial flagellin or EF-Tu might include PRRs for PAMPs indicative for all type of pathogens. Thus, we anticipate that perception of a given PAMP induces the expression of its own receptor as well as a whole set of PRRs for other PAMPs, a process aimed to increase sensitivity to detect pathogens in general. These gene array data also show a general overlap of expression changes after treatment with PAMPs indicative for different types of microbes. Apparently, there is no distinction of the invading microbes based on a signalling signature of PAMPs coming from bacteria, fungi or oomycetes at this level of pathogen perception. Rather, presence of one PAMP appears to be taken as an indication of a danger situation in general and presence of one type of microorganism might serve as indicator of a damaged tissue integrity that might allow entrance of other type of pathogenic microorgansims.

However, differentiation and distinction of pathogens might occur at later steps in host-pathogen interaction. Also, virulence factors of the pathogens differentiate plant defence response. Whereas treatment with all bacteria initially causes similar changes in gene expression as PAMPs, expression of these genes, in contrary, was repressed by virulent bacteria at later time points.

The repertoire of PAMP perception in plants is species-specific. While some PAMPs, like fungal chitin and bacterial flagellin, are perceived by a broad range of species, detection of others seems to be restricted to a more narrow range as for GBP and EIX discussed above. Thus, although the process of innate immune perception is found across species belonging to different kingdoms, the recognition specificities vary and evolve more rapidly even between closely related species (Zipfel and Felix, 2005; Ausubel, 2005). In this work we made use of absence of EF-Tu perception in plants outside the Brasicaceae to test for the function of the *Arabidopsis* EFR gene in transiently transformed *N. benthamiana* leaves. Since these leaves gained responsiveness and also developed binding sites specific for EF-Tu we concluded that EFR is the receptor for this PAMP (FIG. 6). These results also indicate that EFR is the only component missing in *N. benthamiana* for EF-Tu perception.

EFR Perceives a Cytoplasmic Protein of Bacteria

EF-Tu is of fundamental importance for protein translation. It is one of the most conserved proteins, and also the most abundant protein in bacteria (Jeppesen et al., 2005). To exert its prime function, EF-Tu must be located in the cytoplasma of the bacteria and, originally, it came as a surprise that Brassicaceae, like *Arabidopsis*, have a perception system for this cytoplasmic bacterial protein (Kunze et al., 2004). This opens the topological riddle on how this protein from the inside of the bacteria could meet the EF-Tu receptor (EFR) assumed to reside in the plant plasma membrane. In this work we show that mutants defective in EF-Tu perception have a strongly enhanced susceptibility to transformation by T-DNA of *A. tumefaciens*. This gives strong functional evidence that interaction of EF-Tu and EFR indeed occurs in vivo and that this recognition is relevant for plant defence. Whereas this result does not explain the process by which EF-Tu is released from the bacterial cells, examples of processes and conditions that lead to the export of EF-Tu are accumulating in the current literature. EF-Tu has been observed in the secretome of *Xanthomonas campestris, Pseudomonas fluorescens* and *Erwinia* chrysanthemi (Watt et al., 2005; Singh et al., 2004; Kazemi-Pour et al., 2004), or occurring in membrane vesicles termed blebs that are constitutively released from the bacterial outer-membrane in *Neisseria meningitidis* (Post et al., 2005). It has also been found associated with the bacterial surface where it appears to play a role in adhesion to host cells (Dallo et al., 2002; Granato et al., 2004). More interestingly, EF-Tu has even been reported to activate pro-inflammatory responses in human cells (Granato et al., 2004), raising the possibility that EF-Tu might also act as a PAMP in the mammalian innate immune system.

Convergence of EF-Tu and Flagellin Signalling

Although perceived by two different receptors in *Arabidopsis*, flagellin and EF-Tu induce a common set of responses, including rapid medium alkalinization, an oxidative burst, increase of ethylene biosynthesis, a seedling growth inhibition and, most notably, induction of a nearly congruent set of gene. These observations suggest that the early signalling events following the specific perception of these PAMPs rapidly merge into a common downstream signalling pathway.

Previous studies have shown that flg22 treatment induces the activation of a MAP kinase pathway, including MEKK1, MKK4/5 and MPK3/6 (Asai et al., 2002; Nühse et al., 2000). Our MBP in-gel results (FIG. 2) show that flg22 and elf18 activate the same pool of MPK, most probably MPK3 and 6. These MPKs are activated by other PAMPs such as chitin (Nühse et al., 2000; Wan J. et al., 2004) and LPS (Gerber and Dubery, 2004), but also by other biotic or abiotic stimuli (Nakagami et al., 2005), reflecting that they are probably part of a conserved, general stress signalling pathway.

The molecular events linking extracellular perception by plasma membrane receptors to cytoplasmic signalling chains are still unknown. Recent studies on the perception of the brassinosteroid (BR) plant hormones revealed that the LRR-domain of BRI1 is sufficient to bind BR but that it requires an additional LRR-RLK, BAK1, to signal. This opens the possibility that FLS2 and EFR might also interact with other RLKs to induce transmembrane signaling. The EFR intracellular domain is only ~30% similar to FLS2. Therefore, it is currently difficult to infer if FLS2 and EFR interact with the same proteins or not. Future work should answer whether signalling convergence occurs via common adaptors, or via distinct proteins that later converge into a unique signalling pathway.

Perception of EF-Tu and Flagellin Serve Complementary Functions for the Recognition of Bacteria The apparent redundancy in the chemosensory system to detect bacteria opens questions on the interplay and functional integration of the individual detection systems. Additive effects have been reported for combined treatment of *Arabidopsis* with weakly acting elicitor preparations of LPS and PGN (Nürnberger et al., 2004). In our experiments with concomitant application of flagellin and EF-Tu, we could observe additive effects with peptides added at low, non-saturating doses. In contrast, saturating doses of either PAMP stimulated a nearly full response and no clear additive or synergistic effect was detected. A strongly cooperative or synergistic interaction would resemble systems obeying the logic of a Boolean [and], with response only in the presence of two or more stimuli. This type of signal integration might increase safety for severe decisions such as turning on programmed cell death or a hypersensitivity response. Signal integration corresponding to a Boolean [or], in contrast, rather increases sensitivity and ensures detection of a broader spectrum of bacteria. In particular, it renders more hurdles for pathogens to evade recognition systems of the host. Indications for strategies to evade the recognition of flagellin by their hosts have been obtained for bacteria pathogenic to plants and animals. Several plant pathogens have sequence variation in flagellin that renders their flg22-domain non-detectable to FLS2 in *Arabidopsis* (Felix et al., 1999; Pfund et al., 2004) while several bacteria pathogenic for animals have sequence changes in the flagellin-domain recognized by TLR5 in humans (Ramos et al., 2004; Andersen-Nissen et al., 2005). Similarly, the N-terminus of EF-Tu from some plant pathogens like Pst DC3000 and *Xylella fastidiosa* show strongly reduced eliciting activity in *Arabidopsis* (Kunze et al., 2004). Although correlative, this peculiar alterations in this otherwise highly-conserved protein might hint at an evolutionary pressure to modify this part of their EF-Tu protein and avoid recognition by the defence system of the plants.

Despite the redundancy of perception systems observed in innate immunity systems of animals and plants, impairment in perception of a single PAMP has been reported to affect susceptibility in certain instances. In humans, for example, a natural polymorphism in the flagellin receptor TLR5 was associated with enhanced susceptibility to *Legionella pneumophila* (Hawn et al., 2003), and lack of functional TLR11 was recently associated with human diseases provoked by uropathogenic bacteria and the protozoan *Toxoplasma gondii* (Zhang et al., 2004; Yarovinsky et al., 2005). Similarly, *Arabidopsis* plants lacking the flagellin receptor FLS2 are more susceptible to Pst DC3000 (Zipfel et al., 2004) and, as described in this report, mutants in EF-Tu perception prove more susceptible to transformation by *Agrobacterium tumefaciens*.

The Efficiency of *Agrobacterium*-Mediated Plant Transformation is Inhibited by Activation of Plant Basal Defences

*Agrobacterium tumefaciens* causes crown gall on many plant species (Escobar and Dandekar, 2003) by an infection process involving transfer and integration of a part of its DNA, the transferred-DNA (T-DNA), into the plant genome.

Many years of research have focused on different aspects of the *Agrobacterium*-host interaction, such as cell-cell recognition and cell-to-cell transport, nuclear import, assembly and disassembly of protein-DNA complexes, DNA recombination, and regulation of gene expression (Gelvin, 2003; Tzfira et al., 2004). However, the extent to which *Agrobacterium* is initially recognized as a pathogen and the potential effect of plant defence responses on transformation efficiency have received little attention. We found that *Arabidopsis* plants mutated in their EF-Tu receptor express ~10-fold more GUS activity than wild-type when transformed with *Agrobacterium* carrying this reporter gene. Reciprocally, we found that addition of active EF-Tu- or flagellin-derived peptides to the *Agrobacterium* inoculum almost completely suppresses plant transformation. Theoretically, these differences in GUS activity could also arise from PAMP-induced defence processes that lead to inhibition of transgene expression. However, transformation assays using a lower and limiting inoculum of *Agrobacterium* indicated that it is indeed the number of transformation sites/events that differs between wild type and efr mutants rather than the intensity of the staining of the individual sites.

In our experiments with wild type and efr mutants *Agrobacterium* injected at different initial concentrations usually did not multiply more than 10-fold within 4 to 10 days post-infection (data not shown). Surprisingly, the enhanced level of plant transformation in efr mutants, as well as the development of disease symptoms at later time points, did not correlate with significantly higher *Agrobacterium* growth. This suggests that the number of bacteria is probably not what limits plant transformation in the wild type, and provides another example where bacterial-triggered disease symptoms can be uncoupled from bacterial growth (Bent et al., 1992).

These results clearly demonstrate that perception of *Agrobacterium* by the plant defence system restricts its ability to transform plant cells. Interestingly, recent studies show that *Agrobacterium* induces plant defence gene expression (Ditt et al., 2005; Ditt et al., 2001; Veena et al., 2003). In addition, the *Arabidopsis* cep1 mutant that constitutively expresses defence-related genes is more resistant to *Agrobacterium* infection (Zhu et al., 2003).

Although these results already suggested that activation of plant defences by *Agrobacterium* could inhibit transformation, the identity of the bacterial and plant molecule(s)

involved in these responses was still unknown. Our work clearly demonstrates a role for EF-Tu perception in restricting *Agrobacterium* infection. It is interesting to note that *N. benthamiana* plants, which belong to the Solanaceae, do not respond to EF-Tu (Kunze et al., 2004) and are highly sensitive to *Agrobacterium* infection (Joh et al., 2005). However, *Agrobacterium* probably display additional PAMPs that are recognized by *Arabidopsis* and/or other plant species. In particular, we found that efr plants were still responsive to *Agrobacterium* extracts (G.F., unpublished data). Based on the current knowledge of PAMP perception in plants we anticipate that differences in transformation efficiency observed between plant genotypes or species could be explained by their different responsiveness to PAMPs.

There are at least four steps at which plant defence processes could interfere with the *Agrobacterium*-mediated transformation process: These steps include bacterial attachment to the plant cell surface; transfer of the T-DNA into the plant cell and then into the nucleus, and, finally, stable integration of T-DNA into the plant genome (Gelvin, 2003). The transient expression assay used in our study does not necessarily involve this last step of stable integration of the T-DNA into the plant genome. However, since our results indicate that at least one of the earlier steps get blocked by the plant innate immune system we anticipate that this defence response will also affect the frequency of stable transformation. Future studies will address this question that is also of practical interest to the genetic engineers. Many crop species remain difficult to transform with *Agrobacterium*. Therefore, our findings enable manipulation of plant defences in recalcitrant plants to allow more efficient transformation by *Agrobacterium*.

Additionally to the methods described above, the data given in the Examples below shows that inhibitors of callose deposition, such as xanthan gum and 2-deoxy-D-Glucose (2-DDG) can increase the efficiency of transient GUS expression. These can thus be used independently of, or in conjunction with, other methods of the present invention to enhance plant transformation efficiency, for example by performing the transformation of said plant with a bacterium in conjunction with an effective concentration of an inhibitor of xanthan deposition. As shown in the Example below, a 3-4 fold increase in *Agrobacterium* transformation efficiency in the presence of about 150 micrograms per ml of Xanthan or 250 micromolar 2-DDG has been found where these compounds are administered in a particular regimen of pre-treatment (e.g. 24 hours prior to transformation) and\or mixed with the bacterium. Preferred methods of the invention may thus utilise Xanthan gum at a concentration of at least about 150 micrograms per ml and\or 2-DDG at a concentration of at least about 250 μM.

Having described this invention in detail above, the following examples are provided to further describe this invention, including its best mode, and to fully enable those skilled in the art to practice this invention. However, the invention should not be considered to be co-extensive with the specifics of the examples provided here. Rather, for this purpose, reference should be made to the appended claims, and the equivalents thereof.

The disclosure of all documents, patents, publications and other references made herein are intended to incorporate such references into the present disclosure as if the entire document, reference, patent, publication or other document which is referred to was fully included herein.

EXAMPLES

In the following examples, the materials and methods used were as follows:

Materials

Peptides were synthesized by F. Fischer (Friedrich Miescher-Institute, Basel, Switzerland) or obtained from Peptron (Daejeon, South-Korea) and peptide solutions were prepared as described previously (Felix et al., 1999; Kunze et al., 2004). Elf18 and elf26 show the same specific activity (Kunze et al., 2004) and were used as fully active EF-Tu-derivatives in the experiments as indicated. Tyr-flg22 and elf26-Tyr-Cys were labelled with [$^{125}$I] iodine at their Tyrosine residues to yield $^{125}$I-Tyr-flg22 ($^{125}$I-flg) and elf26-$^{125}$I-Tyr-Cys (elf-$^{125}$I) with specific radioactivity of 2000 Ci/mmol by Anawa Trading SA (Wangen, Switzerland).

Plant Growth Conditions

*Arabidopsis thaliana* and *Nicotiana benthamiana* were grown in single pots at 20-21° C. with 65% humidity under ~100 μmol m$^{-2}$ s$^{-1}$ light and 8 h photoperiod in controlled-environment chambers, or on plates containing MS medium (Duchefa), 1% sucrose and 0.8% agar under continuous light (60 μE m$^{-2}$ sec$^{-1}$, Biolux lamps) at 22° C.

Bioassays with Plant Tissue and Cell Cultures

For testing growth inhibition, 5 day old seedlings were transferred to liquid medium as described before (Gómez-Gómez et al., 1999), or they were treated on the agar plates by adding liquid MS containing the peptides to be assayed. The oxidative burst measurements were performed using a luminol based assay (Felix et al., 1999) with leaf tissue in 96-well plates and measuring light emission in a luminometer (MicroLumat LB96P, EG&G Berthold, Switzerland). Ethylene production and induced-resistance experiments were performed as previously described (Felix et al., 1999; Zipfel et al., 2004).

The *Arabidopsis* cell culture was maintained and used for experiments 4-8 days after subculture as described before (Bauer et al., 2001).

For in-gel MBP protein kinase assays proteins were extracted as described (Meindl et al., 1998) and kinase activity was determined after re-naturation of proteins separated by SDS-PAGE containing 0.2% (w/v) MBP (Sigma) (Suzuki and Shinshi, 1995).

Binding Assays and Chemical Crosslinking

Aliquots of cells (~25 mg fresh weight) or plant homogenates were incubated in 0.1 ml binding buffer consisting of 25 mM MES pH 6.0, 10 mM NaCl and 3 mM MgCl$_2$ for assays with $^{125}$I-flg (Bauer et al., 2001) and 25 mM MES pH 6.0, 50 mM NaCl, 10 mM MgCl$_2$, 5 mM KI, 2 mM KCl and 1 mM DTT for assays with elf-$^{125}$I, respectively. In standard assays, samples were supplied with 30 fmol of radiolabeled peptides (2000 Ci/mmol) and the unlabelled peptides used as competitors. Assays to determine the number of binding sites were carried out under conditions close to saturation with 10 nM of the radiolabeled peptides diluted to a specific activity of 66 Ci/mmol with unlabelled peptides. After incubation for the times indicated, unbound radiolabel was removed by filtration as described before (Bauer et al., 2001) except that paper filters Macherey-Nagel NW713 for cells and Whatman 3 mm CHr for plant extracts were used in binding assays with EF-Tu. The radioactivity retained on the filters was measured by γ-counting.

Crosslinking experiments were performed according to (Chinchilla et al., 2006). Briefly, radioligands elf-$^{125}$I and/or $^{125}$I-flg were incubated for 30 min with intact cells or plant extracts as described above. Crosslinking was initiated by addition of 10 μl 25 mM EGS (ethylene glycol bis(succinimidylsuccinate), Pierce) in dimethylsulfoxide directly to the incubation mixtures containing bound and unbound ligands. After incubation for 30 min at room temperature the reactions were stopped by addition of 20 mM M Tris-HCl (pH 7.5), proteins were separated by SDS-PAGE (7% (w/v) acrylamide) and analyzed using a Phosphor Imager (Molecular Dynamics, Sunnyvale, Calif., USA).

Isolation of T-DNA Insertion Mutants

The EFR T-DNA insertion lines SALK_044334 (efr-1) and SALK_068675 (efr-2) were generated by SIGnAL (Alonso et al., 2003) and obtained from the NASC (Nottingham, UK). To select plants homozygous for the T-DNA insertion, gene-specific primer pairs (forward/reverse) 5'-GCTG-CAGCCACATATCCAGAC-3' (SEQ ID NO: 3)/5'-GGAAGGGTGCCAACAACAGGAG-3' (SEQ ID NO: 4) for efr-1 and 5'-GGATTGCTTGGCCCTGAG-3' (SEQ ID NO: 5)/5'-ACTAGTAGTCTCTCC-3' (SEQ ID NO: 6) for efr-2 were used. Plants yielding no PCR product with the gene-specific primers were subsequently tested for the presence of the T-DNA insertion, using the gene-specific forward primer in combination with the T-DNA left border specific primer LBb1 5'-GCGTGGACCGCTTGCTGCAACT-3' (SEQ ID NO: 7).

Bioinformatic Analysis

Nucleotide and protein sequences were retrieved from the MIPS *Arabidopsis* database or the TIGR *Arabidopsis* database. Prediction of protein domains, localization and other properties were done using programs available on the Expasy website (Gasteiger et al., 2003).

EFR Cloning

A fragment of 7.1 kb including EFR (At5g20480) and 1080 bp upstream the ATG was amplified from Col-0 genomic DNA using the Expand High Fidelity System (Roche) and 5'-TTAACCCGGGGGTGGAACCTGCATCATGTAAAC-3' (SEQ ID NO: 8) as the forward primer and 5'-TAATGG-TACCGCCATAGTATGCATGTCCGTATTTAAC-3' (SEQ ID NO: 9) as the reverse primer. The resulting fragment was subcloned in the pGEM®-T Easy plasmid (Promega). After digestion with NotI, a EFRp::EFR fragment was cloned into the binary vector pGREENII/T-0229 (Hellens et al., 2000). The final construct called pGREENII-EFRp::EFR was verified by sequencing and electroporated into *A. tumefaciens* EHA101 containing the helper plasmid pSOUP. Agrobacterium-Mediated Transient Expression

*Agrobacterium* strains harbouring pGREENII-EFRp::EFR or pCAMBIA2300-FLS2p::FLS2 (Zipfel et al., 2004) were grown in YEB medium overnight at 28° C., diluted into an induction medium (10 mM MES, pH 5.6, 0.1% (w/v) glucose, 0.1% (w/v) fructose, 0.4% (v/v) glycerol, 60 mM $K_2HPO_4$, 33 mM $KH_2PO_4$, 8 mM $(NH_4)_2SO_4$, 2 mM sodium citrate, 1 mM $MgSO_4$, and 50 μM acetosyringone) and grown for additional 4 h until $OD_{600}$ reached 0.4 to 0.5. The *Agrobacterium* cultures were diluted to $OD_{600}$=0.2 in infiltration medium (10 mM MES, pH 5.6, 10 mM $MgCl_2$, and 150 μM acetosyringone), and pressure infiltrated into leaves of 4-5 week-old *N. benthamiana* plants. Infiltrated leaves were analyzed 4 days after injection.

*Agrobacterium*-mediated expression in *Arabidopsis* was performed as described previously (Joh et al., 2005). Briefly, *Agrobacterium* GV3101 strain carrying the GUS-intron transgene in pBIN19g was grown overnight in L medium at 28° C. This culture was diluted 10-fold in fresh L medium and incubated for further 5 h. Bacteria were then collected by centrifugation, resuspended in water at an $OD_{600}$ of 0.4, and injected into leaves of 4-5 week-old *Arabidopsis* plants.

Affymetrix ATH1 Array

Experimental conditions for incubation and treatment of *Arabidopsis* seedlings, total RNA extraction, microarrays hybridizations and statistical analyses were performed as in Zipfel et al. (2004).

Example 1

A High-Affinity Binding Site Specific for EF-Tu on *Arabidopsis* Cells

Suspension cultured *Arabidopsis* cells have been used to establish the structure-activity relationship for various EF-Tu-derived peptides (Kunze et al., 2004). The sensitivity and specificity of these cells for the acetylated N-terminus of the EF-Tu suggested perception via a surface receptor site specific for this novel PAMP. To probe for this site we used an elf26-derivative prolonged at its C-terminus by the amino acid residues Tyr and Cys. When tested for responses in *Arabidopsis* cells, this peptide, either iodinated at its single Tyr or not, exhibited the same specific activity as the two fully active peptides elf26 or elf18. Elf26-Tyr-Cys labelled with $^{125}$Iodine (elf-$^{125}$I) was used to follow kinetics of binding to intact *Arabidopsis* cells (FIG. 1A). Binding reached a maximum within the first 25 min and then remained stable for at least 2 h. Non-specific binding, binding of radiolabel in the presence of a 10 μM excess of non-labelled elf26, stayed low throughout the experiment (FIG. 1A). Adding an excess of elf26 25 min after addition of elf-$^{125}$I did not result in detectable displacement, indicating essentially non-reversible binding of radioligand. Since these experiments were performed at 4° C. this non-reversibility is probably not due to an uptake process.

The affinity and the number of EF-Tu binding sites on intact cells were determined by saturation curves with increasing concentrations of labelled elf-$^{125}$I (FIG. 1B). The values for specific binding accurately fitted to a rectangular hyperbola resulting in an apparent $K_d$ of 0.8 nM and $B_{max}$ corresponding to 2.1 μmol of binding sites per g of cells or, assuming ~4×10$^4$ cells/mg fresh weight (Bauer et al., 2001), to ~3×10$^4$ receptor sites/cell.

The specificity of binding was tested in competitive binding assays with different EF-Tu-derived peptides and the structurally unrelated flg22-peptide (FIG. 1C). Most effective competition, resulting in 50% inhibition of radioligand binding at concentrations of ~10 nM ($IC_{50}$ value), was observed for elf26 and elf18. Whereas these two peptides are fully active as agonists, the shorter peptide elf12 exerts an antagonistic effect (Kunze et al., 2004), and this peptide also competed binding, albeit with an $IC_{50}$ of ~3000 nM. The peptide elf26-Pst, representing the N-terminus of EF-Tu of the plant pathogen *Pseudomonas syringae* pv tomato DC3000 (Pst DC3000), is a much weaker agonist than elf18, and also acts as a less efficient competitor in binding assays ($IC_{50}$ of ~2000 nM, FIG. 1C).

Example 2

Affinity Crosslinking of elf-$^{125}$I Specifically Labels a Polypeptide of ~150 kD Covalent chemical affinity crosslinking of labelled ligands to their binding sites has been successfully used to characterize receptor binding sites for plant- or microbe-derived signal molecules (Matsubayashi and Sakagami, 2000; Scheer and Ryan, 2002; Chinchilla et al., 2006). In experiments with intact cells of *Arabidopsis*, we reproducibly observed specific crosslinking of elf-$^{125}$I to a polypeptide migrating with an apparent molecular mass of ~150 kD on SDS-PAGE (FIG. 1D). In many of the experiments, an additional, weaker band migrating at ~100 kD was labelled as well (FIG. 1D). Labelling of both bands was specific for EF-Tu and could be inhibited by the addition of non-labelled elf26, suggesting that the lower band might be a truncated form or breakdown product of the major 150 kD polypeptide. Crosslinking experiments were performed without washing away unbound ligands, thus demonstrating a high selectivity of the crosslinking between elf-$^{125}$I and the 150 kD polypeptide. Addition of unlabeled elf26 to the crosslinking assays suppressed labelling of the 150 kD polypeptide in a dose-dependent manner with 50% reduction ($IC_{50}$) of labelling at ~4 nM (FIG. 1E). This value is in good agreement with the $IC_{50}$ value for elf26 in competitive binding assays (FIG. 1C). Labelling of the 150 kD protein was dependent on the presence of crosslinker, and no additional band was observed on SDS-PAGE containing a higher acrylamide percentage.

In order to compare the binding sites for EF-Tu with those for flagellin, we performed crosslinking assays with double labelling using elf-$^{125}$I and $^{125}$I-flg on the same cells. Clearly, the 150 kD polypeptide labelled by elf-$^{125}$I is different from the 175 kD band labelled by $^{125}$I-flg (FIG. 1F), which was previously identified as the FLS2 protein (Chinchilla et al., 2006). In summary, EF-Tu interacts specifically with a high-affinity binding site on a ~150 kD polypeptide in *Arabidopsis* cells.

Example 3

EF-Tu and Flagellin Induce a Common Set of Defence Responses

Whereas there are two distinct receptor binding sites, the two PAMPs flagellin and EF-Tu appear to trigger the same set of responses including induction of extracellular alkalinization, an oxidative burst, enhanced ethylene biosynthesis and induced resistance (Zipfel et al., 2004; Felix et al., 1999; Kunze et al., 2004). To test whether the two perception systems would interfere or interact with each other we compared the responses to these PAMPs more closely, and also studied the effects of combined treatments with both PAMPs. Extracellular alkalinization, occurring as a consequence of altered ion fluxes across the plasma membrane, can serve as a rapid, convenient and robust bioassay to characterize qualitative and quantitative aspects of PAMP perception. When challenged with saturating doses of 100 nM of the peptides (FIG. 2A), flg22 induced alkalinization with a time lag of only few seconds, while rise of extracellular pH following elf18 treatment had an apparent lag-phase of ~70 s. In this batch of cells, flg22 reproducibly induced a slightly higher pH-increase than elf18, and co-treatment with flg22 and elf 18 resulted in a response that was not significantly different from the treatment with flg22 alone (FIGS. 2A and 2B). In some batches of the cell culture used for repetitions the maximal alkalinization response induced by the two PAMPs seemed inversed and elf18 induced a slightly higher maximal pH shift than flg22 (data not shown). However, the lag-phase for EF-Tu-derived peptides was always longer than that for flg22, and co-treatment with both peptides never led to significant increase above the response obtained with the stronger of the stimuli alone. However, an additive effect of the two PAMPs was observed in combined application of flg22 and elf18 at non-saturating doses of the elicitors (FIGS. 2A and 2B).

Activation of MAP kinases has been reported as an early signalling event in plants treated with many pathogen- and wound-related stress signals (Nakagami et al., 2005). In-gel assays with myelin basic protein (MBP) as a substrate showed rapid, strong, but transient activation of two MAP kinases migrating with apparent molecular masses of ~48 kD and ~45 kD in cells treated with 100 nM elf18 (FIG. 2C). The same two kinases were likewise induced in cells treated with flg22 (FIG. 2C). As observed above for medium alkalinization, the overall kinetics of induction appeared to be similar for both stimuli, but induction by flg22 was slightly faster than by elf18. In further experiments MAP kinase activity was tested after treatment of cells for 10 min with flg22, elf18 or a combination of both PAMPs (FIG. 2D). No additive effect was detectable for co-treatment with both PAMPs, suggesting that either stimulus alone leads to maximal induction in a common pool of MAP kinases within the cells.

Treatment of *Arabidopsis* leaves with either elf18 or flg22 restricts subsequent growth of virulent Pst DC3000 (Kunze et al., 2004; Zipfel et al., 2004). To test for an additive effect of flagellin and EF-Tu, *Arabidopsis* leaves were pressure infiltrated with 100 nM of either one or both peptides (FIG. 2E). Bacterial growth restriction observed after a combined treatment with both peptides was not more efficient than pre- or co-treatment with one of the peptides alone (FIG. 2E). Prolonging the time of pre-treatment to two days abolished induction of resistance in all of the treatments, indicating that induction of resistance is a transient process. In contrast, addition of the peptides concomitantly with the bacteria induced resistance and restricted bacterial growth by >10-fold (FIG. 2E).

Example 4

Changes in Gene Expression and Number of Receptor Sites after Treatment with EF-Tu and Flagellin Using the whole genome *Arabidopsis* ATH1 array (Affymetrix), changes in mRNA levels of ~1000 genes in response to treatment of *Arabidopsis* seedlings with flg22 has been reported (Zipfel et al., 2004). Using the same experimental conditions, *Arabidopsis* seedlings were treated with EF-Tu-derived peptides for 30 or 60 min. In untreated control seedlings, nearly 13,000 of the 23,000 genes present on the array showed significant level of expression (signal>100). Applying a threshold-filter of 2-fold, 427 genes were up-regulated after 30 min treatment with 1 µM elf26 and this number further increased to 866 after 60 min (FIG. 3A). A >2-fold decrease in mRNA levels was observed for 7 genes after 30 min and 83 genes after 60 min. Changes in the same set of genes was observed in a further series of experiments after treatment of fls2-17 seedlings carrying a mutation in the flagellin receptor gene FLS2 with 1 µM elf18. In contrast, no significant changes in gene expression could be observed after treatment with the inactive peptide elf12. Interestingly, genes induced or repressed by elf26 or elf18 clearly correlate with the ones found to be changed after treatment with flg22 described previously (FIG. 3A, Zipfel et al. 2004).

Among the genes that are rapidly induced after flagellin or EF-Tu treatment, many encode elements potentially involved in signal perception and transduction (Zipfel et al., 2004). In particular, a high percentage of genes encoding RLKs were induced by treatment with both PAMPs. In the experiments described above, 262 of the 610 RLKs present in the genome (Shiu et al., 2004) showed measurable levels of expression and up to 105 of these genes were >2-fold induced after treatment with EF-Tu and flagellin. Interestingly, the flagellin receptor FLS2 (At5g46330) is induced after treatment with flagellin or EF-Tu. We wondered whether the increased level of FLS2-mRNA results in an increased level of receptor sites for flagellin and, whether the number of receptor sites for EF-Tu would change in parallel. Flg22 and elf18 interact with their corresponding binding sites in a non-reversible manner which impedes accurate determination of flagellin binding sites after flagellin treatment and EF-Tu binding sites after EF-Tu treatment, respectively. Thus, we tested the number of binding sites for flagellin after pretreatment with elf18 (FIG. 3B) and, vice versa, the number of EF-Tu-binding sites after pretreatment with flagellin (FIG. 3C). Indeed, in both cases, the number of specific binding sites significantly increased after 1 to 2 h of pretreatment and reached a level >2-fold higher than controls within 4 to 6 h of treatment. Similar, >2-fold increases in specific receptor sites were also observed in cultured cells treated with flg22 or elf18 (data not shown), thus corroborating the finding that stimulation with one of the PAMPs increases the number of receptor sites for the other PAMP. These results confirm our initial hypothesis that the perception of one PAMP might lead to enhanced expression of a whole set of PAMP receptors and, more specifically, that the receptor for EF-Tu might be present among the genes induced by both PAMPs.

Example 5

Identification of a Mutant Insensitive to EF-Tu Treatment

EF-Tu perception shares many features with perception of flagellin. Both PAMPs are peptides which activate their receptors in a two step process according to the concept of address-message (Bauer et al., 2001; Kunze et al., 2004). Also, both receptor sites are up-regulated after stimulation with one of the PAMPs (FIGS. 3B and 3C). Thus, we speculated that perception of EF-Tu might involve a RLK gene related to FLS2 and that belongs to the group of RLKs induced after stimulation with both PAMPs. Starting with close relatives of FLS2 we established a collection of homozygous T-DNA-tagged mutants for induced LRR-RLKs from lines provided by the Salk collection (Alonso et al., 2003). These mutant lines were then tested for response to EF-Tu using the seedling growth inhibition assay that has been successfully employed previously to screen for flg22-insensitive mutants (Gómez-Gómez and Boller, 2000). Treatment with elf18 led to strong growth-inhibition in seedlings of wild-type Col-0 and all of the mutant lines except the line SALK_044334, which proved completely insensitive to elf18 (FIG. 4A and FIG. 1G). However, seedlings of line SALK_044334 were as sensitive to treatment with flg22 as wild-type seedlings, suggesting that this line is specifically affected in EF-Tu perception. Similarly, treatment of these mutant plants with elf18 did not induce an oxidative burst while a full response was observed after treatment with flg22 (FIG. 4B). In comparison, fls2 mutants affected in the flagellin receptor FLS2 showed normal responses to elf18 but lacked responses to flg22 (FIGS. 4A and 4B). Treatment of the line SALK_044334 with EF-Tu-derived elicitors did not cause enhancement of ethylene biosynthesis and it also did not trigger induced resistance to infection by the virulent bacterium Pst DC3000 (FIG. 1G). Apart from lack of responses to EF-Tu-derived elicitors, this line was indistinguishable from wild-type plants and no other phenotype became apparent over several generations.

When assayed for the presence of receptor binding sites for EF-Tu, specific binding was detectable in extracts from wild-type plants but not in extracts from SALK_044334 plants (FIG. 4C). Similarly, crosslinking experiments with elf-$^{125}$I on SALK_044334 plant extracts did not label the two polypeptides (~150 and ~100 kD) that get specifically labelled in extracts from wild-type plants (FIG. 4D).

In summary, SALK_044334 plants proved completely insensitive to EF-Tu but exhibited normal responses to flg22 in all bioassays, suggesting that this mutant is affected in a function specifically required for EF-Tu perception.

Example 6

EFR is the EF-Tu Receptor

SALK_044334 plants carry a T-DNA insert in At5g20480, which was tentatively termed EFR for EF-Tu receptor (FIG. 5A). No mRNA encoding EFR was detectable in SALK_044334 (renamed efr-1) plants by RT-PCR (data not shown). Linkage of EF-Tu-insensitivity with this gene was confirmed with the line SALK_068675 (efr-2) which carries an insert in the same gene (FIG. 5A) and proved as insensitive to treatment with elf18 as efr-1 (data not shown). Complementation of SALK_044334 (efr-1) with wild-type EFR restored full responsiveness to elf18. All together, these results show that the EFR gene is essential for EF-Tu perception.

The EFR gene codes for a LRR-RLK of the subfamily XII, which also comprises FLS2 and 8 additional members (Shiu and Bleecker, 2001b). No biological function has been assigned to this gene so far. The gene encodes a predicted protein of 1031 amino-acids residues with a molecular mass of 113 kD and all characteristic of a LRR-RLK (FIG. 5C). It has a hydrophobic N-terminus predicted to act as a signal peptide for secretion, an extracellular domain with 21 tandem copies of a 24-residue LRR (residues 96 to 606) with the consensus sequence LxxLxxLxLxxxNxLxGxlPxxLGx (SEQ ID NO: 2). Unlike in other plant LRR-RLKs, the LRR region of EFR is not interrupted by an "island" domain (Dievart and Clark, 2003). The LRR domain is flanked by pairs of Cys with the characteristic spacing observed in several of the LRR-RLKs (Dievart and Clark, 2003). A single trans-membrane domain (residues 650 to 673) is predicted to separate the extracellular from the intracellular domain which shows all the signatures of a serine-threonine protein kinase (residues 712 to 1000) (Hanks and Quinn, 1991). Similar to the related flagellin receptor FLS2, EFR might be glycosylated at some of its 21 potential N-glycosylation sites (N—X—S/T) in its extracellular LRR-domain. Thus, the 150 kD band that shows specific crosslinking with elf-$^{125}$I might correspond to the glycosylated EFR protein (FIGS. 1C and 4D). With these structural features EFR is a primary candidate for the receptor of the EF-Tu.

*Nicotiana benthamiana* plants, as all plants outside the family of Brassicaceae tested so far, are non-responsive to EF-Tu (Kunze et al., 2004). To test whether this is due to a lack of functional EFR, we transiently expressed EFR under the control of its native promoter in *N. benthamiana* leaves by agroinfiltration (Van der Hoorn et al., 2000). Transformation with EFR resulted in specific binding of elf-$^{125}$I peptide while plants agroinfiltrated with a control construct (AtFLS2) showed no binding of EF-Tu./Transformation with EFR but not with the control construct (AtFLS2) resulted in specific binding sites detectable by crosslinking with $^{125}$I peptide (FIG. 6A). Labelling of the two proteins migrating with ~xxx kD and ~xxx kD on SDS-PAGE was fully inhibited in the presence of unlabelled elf peptide added as a competitor. Importantly, the leaves expressing the EFR gained responsiveness to EF-Tu, as illustrated with induction of an oxidative burst (FIG. 6B) and enhanced biosynthesis of ethylene (FIG. 6C). No induction of these responses was observed after treatment with the inactive elf12 peptide (FIGS. 6B and 6C). Also, no response to elf18 was observed in non-transformed leaves or in leaves transformed with the control construct encoding AtFLS2 (FIGS. 6B and 6C).

In summary, these results demonstrate that EFR encodes a functional binding site for EF-Tu that is also capable to activate signalling and induce physiological responses in *Arabidopsis*, but also when expressed in *N. benthamiana* plants.

Example 7

EF-Tu Perception Limits *Agrobacterium tumefaciens* Infection

PAMP-perception by plants is thought to play a role in induction of basal resistance and restriction of microbial infection. For example, the fls2-mutants lacking a functional flagellin receptor are more susceptible to spray inoculation with the bacterium Pst DC3000 (Zipfel et al., 2004). In contrast, the efr mutants described here showed the same susceptibility as wild type when infected with Pst DC3000 by spraying or injecting with a syringe. However, whereas Pst DC3000 has a flagellin that is fully active as PAMP in *Arabidopsis*, its EF-Tu has a N-terminal amino-acid sequence that exhibits only strongly reduced elicitior-activity (Kunze et al., 2004). This renders this pathogen not suitable for testing the role of EF-Tu perception in activation of basal resistance. In contrast, the plant pathogen *Agrobacterium tumefaciens* has a modified flg22-epitope in its flagellins that cannot be detected by sensing system of plants (Felix et al., 1999) but the N-terminus of its EF-Tu protein is fully active as an elicitor in *Arabidopsis* (Kunze et al., 2004).

*A. tumefaciens* infects its host via wound sites and, rather than being a rapidly multiplying foliar pathogen, causes the crown gall disease characterized by a slow but persistent infection. This infection process critically depends on the transfer of a small part of the bacterial DNA, termed T-DNA, into the genome of the plant hosts (Escobar and Dandekar, 2003; Gelvin, 2003). The transfer of T-DNA into the plant cells occurring during the initial phase of the infection process can serve as a convenient readout for the success of *A. tumefaciens* to infect its host. To test if EF-Tu perception plays a role in restricting *A. tumefaciens* infection, wild-type (Col-0) and efr-1 leaves were injected with the hyper-virulent non-tumorigenic strain of *A. tumefaciens* (GV3101) harbouring a binary plasmid containing a β-glucuronidase (GUS)-intron construct that allows expression in plants but not in bacteria. In Col-0 leaves only a weak activity of GUS was detectable at 2 or 4 days post-infection (dpi) (FIG. 7A). In contrast, efr-1 leaves exhibited intense GUS staining already at 2 dpi. Also, as confirmed in several independent repetitions of this experiment, Col-0 leaves showed considerable leaf-to-leaf variation while transformation of the efr-1 mutant was always higher and more uniform (FIG. 7A). The allelic mutant line efr-2 exhibited the same enhancement of transformation as efr-1, and complementation of efr-1 with the wild-type EFR gene resulted in plants with the low level of GUS expression found in wild type. Quantitative analyses of GUS activity in extracts from infiltrated leaves at 4 dpi revealed about 10-fold more GUS activity in leaves of efr-1 than leaves of wild-type (FIG. 7B). In independent repetitions of this quantitative experiment (n=XX) enhancement of GUS in efr mutants over wild type varied from xx to ~20-fold. Interestingly, the increase in plant transformation in efr mutants did not correlate with a significant increase in number of *A. tumefaciens* bacteria found in these leaves. However, whereas inoculation of *A. tumefaciens* into *Arabidopsis* wild-type leaves did not cause any visual disease symptoms, about half of the infiltrated efr-1 leaves developed clear disease symptoms within one week after inoculation (FIG. 7C).

These results clearly indicate a role for EFR in restricting *Agrobacterium*-mediated transformation and they strongly suggest that this occurs via perception of EF-Tu by EFR. To confirm that PAMP-dependent activation of plant defences lowers transformation efficiency, we measured GUS activity in leaves injected *A. tumefaciens* in combination with saturating doses of flg22 or elf18. Indeed, co-injection of 1 µM flg22 or 1 µM elf18 nearly abolished GUS expression in leaves of wild type (FIG. 7B). Similarly, in efr-1 leaves flg22 strongly reduced transformation while elf18 did not affect transformation in this mutant line (FIG. 7B). These results show that defence responses activated by PAMPs restrict plant transformation by *A. tumefaciens*. In particular, they also give functional evidence that EF-Tu from the bacteria gets perceived by EFR in planta, and that this perception process is physiologically relevant to limit bacterial attack.

Example 8

Bacterial Strains

Disarmed *A. tumefaciens* C58C1 was used for bacterial growth curves, transformed with pTFS40 (empty vector), pMDA-35S::avrPto, pT50-35S::avrPtoB, pTA7002-Dex:: avrPtoG2A, pVSP61-35S::avrRPS4 and pMAQ-35S::aequorin.

Transient and Nonhost HR Assay

For elicitation of the HR, purified flagellin or INF1 were infiltrated (at 100 µg/ml) in the first fully expanded leaf of three to four week-old plants. *A. tumefaciens* mediated transient expression was performed as described previously [1]. The tissue was usually used for further experimentation 2 dpi.

Measurement of ROS Generation

Leaf discs ($3*0.38$ $cm^2$/well) were floated on $H_2O$ overnight. To measure the accumulation of ROS, reactive oxygen species released by the leaf tissue were measured by a luminol-dependent assay [2]. The $H_2O$ was replaced with 500 µl of a solution containing 20 µM luminol (SIGMA) and 1 µg horseradish peroxidase (Fluka). The luminescence was measured at 10 min after elicitation with either 10 µg/ml PtabF or 50 ng Csp22 using the Photek camera system, since elicitation reached a steady state level by this time.

Measurement of Calcium Influx

An intracellular increase of calcium was measured by *Agrobacterium*-mediated transient expression of 35S:aequorin [3]. Leaf discs ($2*0.38$ $cm^2$/well) were floated on $H_2O$ containing 2.5 µM coelentherazine overnight in the dark and at room temperature, and luminescence was measured after elicitation with10 µg/ml PtabF using the Photek camera system.

Protein Extraction and Immunoblotting

The frozen tissue was ground in liquid nitrogen and the powder mixed with two volumes of extraction buffer (50 mM Tris-HCl pH 7.5, 150 mM NaCl, 5 mM EDTA, 2 mM DTT, 5% glycerol, 1% polyvinylpolypyrrolidone, plant protease inhibitor cocktail from SIGMA) was added and the mixture kept on a rotation wheel for 30 min at 4° C., followed by 5 min centrifugation at 15500 g. The supernatant was assayed directly or flash-frozen and stored at −80° C. The protein content was quantified using the Bradford dye-binding assay. Extracted proteins (~80 µg total protein from leaves) were fractionated by 10% SDS-PAGE for visualization of SIPK activation, and transferred onto Hybond™-P membranes (Amersham). Polyclonal phospho-specific MAPK (anti-pERK, p44) antibody (New England Biolabs) raised against a peptide which corresponds to amino acids 305-327 of ERK-1 was used as a primary antibody. Peroxidase-conjugated goat anti-mouse IgG (Dako) was used as the secondary antibody. MAPKs were visualized using an enhanced chemiluminescence protocol according to the manufacturer's directions (Amersham). Extracted proteins for visualization of AvrPto and AvrPtoB-HA were separated by 12% SDS-PAGE. For AvrPto detection a polyclonal antibody raised against AvrPto-GST in rabbit was used as the primary antibody, with a peroxidase-conjugated goat anti-rabbit IgG (Pierce) as the secondary antibody. For detection of AvrPtoB an anti-HA epitope tag antibody (Roche) was used as a primary antibody, fallowed by a peroxidase-conjugated goat anti-rat (Pierce) antibody as a secondary antibody.

Callose Deposition

Callose deposition was analyzed 24 h post infiltration of either 10 µg/ml PtabF or 10 µg/ml of INF1 according to Hauck et al. [4]. The images were taken at a magnification of 5×0.16. 5 pictures per sample were analyzed using the PDQuest software and average to give representative values of callose deposits per square centimetre.

Bacterial Growth Curves

For bacterial growth curves, A. tumefaciens strain C58C1 transformed with binary vectors for transient expression of different effector genes was grown overnight in Lennox (L) medium containing the appropriate antibiotics and incubated at 28° C. Bacterial suspensions in 10 mM $MgCl_2$ were infiltrated at $2\times10^7$ CFU/ml using a needleless syringae. Leaf discs were harvested at 0 days post inoculation (dpi), at 2 dpi and at 4 dpi and ground in 10 mM Mg $Cl_2$.

The CFU per square centimetre were determined by plating serial dilutions of leaf extracts on L agar plates containing the appropriate antibiotics. Each data point represents average bacterial numbers of three replicates and error bars indicate standard deviations. The experiments were repeated at least three times with similar results and representative results are shown.

Purification of Flagellin from P. syringae and A. tumefaciens

Monomeric flagellin was purified according to [5] from P. syringae DC3000 (PtomF), P. syringae pv tabaci (PtabF) and the A. tumefaciens lab strain GV3101 (AtumF). The purity of the sample was confirmed by silverstaining after separation by 12% SDS-PAGE. The identity of the sample was proven by LTQ mass spectrometry.

Purification of INF1

To prepare Phytophtora infestans elicitin (in f gene product), overnight cultures of E. coli cells, DH5α carrying a chimeric plasmid (pFB53) with inf1 gene [6] were diluted (1:100) in Luria-Bertani medium containing ampicillin (50 µg·mL$^{-1}$) and incubated at 37° C. When the $OD_{600}$ of cultures reached 0.6, elicitin was induced into cultured medium by the addition of 0.4 mM IPTG for overnight. The supernatant was collected by centrifugation, and filtrated by a 0.45 µm pore syringae filter disk (Solerius) to eliminate E. coli. The preperation was kept at −20° C. and used as elicitin.

Silencing

Silencing was performed as described elsewhere [7].

1. Sessa, G. and G. B. Martin, Signal recognition and transduction mediated by the tomato Pto kinase: a paradigm of innate immunity in plants. Microbes Infect, 2000. 2(13): p. 1591-7.
2. Keppler, L. D., Baker, C. J., and Atkinson, M. M., Phytophatology, 1989. 79: p. 974-978.
3. Knight, H., A. J. Trewavas, and M. R. Knight, Cold calcium signaling in Arabidopsis involves two cellular pools and a change in calcium signature after acclimation. Plant Cell, 1996. 8(3): p. 489-503.
4. Hauck, P., R. Thilmony, and S. Y. He, A Pseudomonas syringae type III effector suppresses cell wall-based extracellular defense in susceptible Arabidopsis plants. Proc Natl Acad Sci USA, 2003. 100(14): p. 8577-82.
5. Taguchi, F., Shimizu, R., Nakajima, R., Toyoda, K., Shiraishi, T., and Ichinose, Y., Differential effects of flagellins from Pseudomonas syringae pv. tabaci, tomato and glycinea on plant defense response. Plant Physiology and Biochemistry, 2003. 41(2): p. 165-174.
6. Kamoun, S., et al., A gene encoding a protein elicitor of Phytophthora infestans is down-regulated during infection of potato. Mol Plant Microbe Interact, 1997. 10(1): p. 13-20.
7. Peart, J. R., et al., An EDS1 orthologue is required for N-mediated resistance against tobacco mosaic virus. Plant J, 2002. 29(5): p. 569-79.

Results

Common defence responses induced by PAMPs (pathogen associated molecular patterns that elicit defense response in plant cells) are summarized in Table A:

TABLE A

Responses induced by different PAMPs in N. benthamiana

| | Flagellin | INF1 | Csp-22 | LPS |
|---|---|---|---|---|
| ROS | X | X | X | X |
| Callose deposition | X | X | ? | X |
| MAPK activation | X | X | X | ? |
| Calcium burst | X | ? | X | X |
| HR | X | X | — | — |

The earliest responses include an increase in cytosolic Calcium (Calcium burst), the generation of reactive oxygen species (ROS), phosphorylation of mitogen activated protein kinases (MAPK activation) & the deposition of callose into the cell wall. x indicates induction of this response in N. benthamiana, - means that this response was not induced & ? means untested.

FIG. 8. Suppression of PtabF-induced ROS by AvrPto and AvrPtoB in N. benthamiana; AvrPto-G2A is a defective mutant of AvrPto. AvrPto and AvrPtoB are unrelated; Photon counts indicates the increase in ROS (the higher the more ROS is produced); represents 6 independent experiments, averaged at t=600 s; leaf tissue transiently expressing the P. syringae effector proteins AvrPto, AvrPtoB and AvrRPS4; PtabF induced. Similar pattern For PtomF, flg22 & CSP22; AvrPto and AvrPtoB also suppress calcium burst in a similar fashion.

FIG. 9. Suppression of callose-deposition and MAPK activation by AvrPto & AvrPtoB; All in N. benthamiana; Top left: Suppression of callose deposition (light spots) by avrPto (stable transgenic N. benthamiana). Top right panel: quantitation of callose deposits (black: induced with flagellin & white induced with INF1); lower part: Western Blot to detect activated SIPK (a MAP Kinase from N. benthamiana). Left is the negative control where water was used for the elicitation & right (+) flagellin used for the elicitation; Anti-pERK1-2 Western blot for detection of MAPK activation; —=uninduced; +=induced with PtabF; –>similarly for INF1, CSP22, PtomF & flg22.

FIG. 10. Nonhost HR induced by flagellin; Flagellin from Pseudomonas syringae induces a so-called nonhost HR on Solanaceous species; No flagellin HR in Arabidopsis; Flagellin was also found to induce the HR in rice; Flagellin from Pseudomonas syringae induces a nonhost HR on Solanaceous species—here: 76R=tomato & N. b. =N. benthamiana.

A gel on the flagellin purification demonstrated that the sample was highly pure (mass spec & silver staining).

FIG. 11. AvrPto and AvrPtoB suppress the HR induced by flagellin; AvrPto & AvrPtoB suppress this nonhost HR in tomato & *N. benthamiana*; Similar results with INF1

FIG. 12. AvrPto and AvrPtoB act as pathogenicity factors and allow *A. tumefaciens* to grow on *N. benthamiana*. AvrPto & AvrPtoB can enhance the growth of *Agrobacterium* (C58C1) when transiently expressed (by the same Agro strain) in *N. benthamiana*. This means that there is a PAMP other than EF-Tu (which is not recognized in *N. benthamiana*), that restricts growth of *Agrobacterium* in *N. benthamiana*. Y axis=log cfu/square cm.

FIG. 13. Suppression of oxidative burst in *Arabidopsis* by AvrPto; The exact same result was achieved with AvrPtoB. Western Blot confirms the expression of the protein. The fluorescence provided a visual readout of the ROS measurement (light blue circles showed the accumulation of ROS in the periphery of a leaf disc). The excel graph is a quantitative readout of the same experiment.

Example 9

The chemical 2-DDG is a well-known inhibitor of callose biosynthesis (Jaffe and Leopold, 1984; Ton and Mauch-Mani, 2004). Xanthan, an exopolysacharide from *Xanthomonas* sp., has been shown to be an essential virulence factor capable of inhibiting callose deposition in the host plants (Yun et al., 2006).

These chemicals were therefore tested in the transformation enhancement tests.

Initial qualitative GUS staining after co-infiltration of xanthan gum with GV3101-GUS seemed encouraging, although the levels of expression in control leaves was very low compared to previous control experiments.

In one experiment, quantitative measurement of GUS expression did not reveal statistically significant improvement following low concentrations (less than 100 µg/ml). of xanthan gum co-infiltration (results not shown).

We therefore tested the effect of higher xanthan gum concentrations by co- or pre-infiltration treatments (FIG. 14-16). At 150 µg/ml, xanthan gum greatly enhanced the level of GUS expression in treated leaves.

Concentrations of xanthan gum higher than 150 µg/ml did not lead to further improvement (FIG. 15). This could be easily explained by the fact that the xanthan gum solution becomes then too viscous to allow efficient infiltration or uptake by the plant tissues.

The effect was highest (4-fold improvement) when xanthan gum was sprayed onto the leaves one day prior to *Agrobacterium* infiltration (FIG. 16), probably as it reduced the wounding stress triggered by two successive infiltrations.

At the commonly used concentration of 250 µM, 2-DDG also seemed to improved the level of GUS expression when sprayed one day prior to *Agrobacterium* infiltration (FIG. 16)., corroborating a role of callose deposition in defense against *Agrobacterium*.

Finally, in FIG. 17 we tested tested a possible additive or synergistic effect of xanthan gum and 2-DDG in improving GUS expression. In addition, we tested whether addition of the chemicals in the *Agrobacterium* inoculum following spraying of the same chemicals one day prior to infiltration led to further enhancement of transient GUS expression. Spray pre-treatment did not give as much enhancement as observed earlier, but still gave little enhancement over control. However, combining a spray pre-treatment with co-infiltration significantly enhanced the level of GUS expression. The level of enhancement was similar for both 2-DDG and xanthan gum individually and together, emphasizing that they are acting on the same process i.e. callose deposition. This suggests a condition where repeated suppression of basal defense (in this case callose deposition) will facilitate *Agrobacterium*-mediated transformation.

It is also important to note that we used here commercially available xanthan gum from Sigma that might not be pure, nor represent the most active fraction of xanthan. The use of purified xanthan from *Xanthomonas* (for example as used in Yun et al. (2006)) might reveal a yet more pronounced effect of xanthan treatment.

Additional Discussion

Down Regulation

The identification of the EFR as described above has implications for its use, for example in the aspects of the invention concerned with enhancing the plant transformation efficiency of a bacterium which comprises. Likewise FLS, to which the following discussion applies mutatis mutandis.

In particular it may be desirable to down-regulate this gene in a plant which it is desired to transform.

In using anti-sense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al., (1988) *Nature* 334, 724-726; Zhang et al, (1992) *The Plant Cell* 4, 1575-1588, English et al., (1996) *The Plant Cell* 8, 179-188. Antisense technology is also reviewed in Bourque, (1995), *Plant Science* 105, 125-149, and Flavell, (1994) *PNAS USA* 91, 3490-3496. Appropriate nucleic acid can be introduced into plant cells using any suitable technology, such as particle or microprojectile bombardment (U.S. Pat. No. 5,100,792, EP-A-444882, EP-A-434616) microinjection (WO 92/09696, WO 94/00583, EP 331083, EP 175966, Green et al. (1987) *Plant Tissue and Cell Culture*, Academic Press), electroporation (EP 290395, WO 8706614 Gelvin Debeyser) other forms of direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, PNAS U.S.A. 87: 1228 (1990d) Physical methods for the transformation of plant cells are reviewed in Oard, 1991, *Biotech. Adv.* 9: 1-11.

An alternative to anti-sense is to use a copy of all or part of the target gene inserted in sense, that is the same, orientation as the target gene, to achieve reduction in expression of the target gene by co-suppression. See, for example, van der Krol et al., (1990) *The Plant Cell* 2, 291-299; Napoli et al., (1990) *The Plant Cell* 2, 279-289; Zhang et al., (1992) *The Plant Cell* 4, 1575-1588, and U.S. Pat. No. 5,231,020. Further refinements of the gene silencing or co-suppression technology may be found in WO95/34668 (Biosource); Angell & Baulcombe (1997) The EMBO Journal 16, 12:3675-3684; and Voinnet & Baulcombe (1997) Nature 389: pg 553.

Further options for down regulation of gene expression include the use of ribozymes, e.g. hammerhead ribozymes, which can catalyse the site-specific cleavage of RNA, such as mRNA (see e.g. Jaeger (1997) "The new world of ribozymes" Curr Opin Struct Biol 7:324-335, or Gibson & Shillitoe (1997) "Ribozymes: their functions and strategies form their use" Mol Biotechnol 7: 242-251.)

The complete sequence corresponding to the coding sequence (in reverse orientation for anti-sense) need not be used. For example fragments of sufficient length may be used. It is a routine matter for the person skilled in the art to screen fragments of various sizes and from various parts of the coding sequence to optimise the level of anti-sense inhibition. It may be advantageous to include the initiating methionine ATG codon, and perhaps one or more nucleotides upstream of the initiating codon. A further possibility is to target a conserved sequence of a gene, e.g. a sequence that is characteristic of one or more genes, such as a regulatory sequence.

The sequence employed may be about 500 nucleotides or less, possibly about 400 nucleotides, about 300 nucleotides, about 200 nucleotides, or about 100 nucleotides. It may be possible to use oligonucleotides of much shorter lengths, 14-23 nucleotides, although longer fragments, and generally even longer than about 500 nucleotides are preferable where possible, such as longer than about 600 nucleotides, than about 700 nucleotides, than about 800 nucleotides, than about 1000 nucleotides or more.

It may be preferable that there is complete sequence identity in the sequence used for down-regulation of expression of a target sequence, and the target sequence, although total complementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a variant of such a sequence in the terms described above. The sequence need not include an open reading frame or specify an RNA that would be translatable.

Anti-sense or sense regulation may itself be regulated by employing an inducible promoter in an appropriate construct.

Double stranded RNA (dsRNA) has been found to be even more effective in gene silencing than both sense or antisense strands alone (Fire A. et al Nature, Vol 391, (1998)). dsRNA mediated silencing is gene specific and is often termed RNA interference (RNAi) (See also Fire (1999) *Trends Genet.* 15: 358-363, Sharp (2001) *Genes Dev.* 15: 485-490, Hammond et al. (2001) *Nature Rev. Genes* 2:1110-1119 and Tuschl (2001) *Chem. Biochem.* 2: 239-245).

RNA interference is a two step process. First, dsRNA is cleaved within the cell to yield short interfering RNAs (siRNAs) of about 21-23 nt length with 5' terminal phosphate and 3' short overhangs (~2 nt) The siRNAs target the corresponding mRNA sequence specifically for destruction (Zamore P. D. Nature Structural Biology, 8, 9, 746-750, (2001)

Thus in one embodiment, the invention provides double stranded RNA comprising a EFR-encoding sequence, which may for example be a "long" double stranded RNA (which will be processed to siRNA, e.g., as described above). These RNA products may be synthesised in vitro, e.g., by conventional chemical synthesis methods.

RNAi may be also be efficiently induced using chemically synthesized siRNA duplexes of the same structure with 3'-overhang ends (Zamore P D et al Cell, 101, 25-33, (2000)). Synthetic siRNA duplexes have been shown to specifically suppress expression of endogenous and heterologeous genes in a wide range of mammalian cell lines (Elbashir S M. et al. Nature, 411, 494-498, (2001)).

Thus siRNA duplexes containing between 20 and 25 bps, more preferably between 21 and 23 bps, of the EFR sequence form one aspect of the invention e.g. as produced synthetically, optionally in protected form to prevent degradation.

Alternatively siRNA may be produced from a vector, in vitro (for recovery and use) or in vivo.

Preferably the nucleic acid in the vector is under the control of, and operably linked to, an appropriate promoter or other regulatory elements for transcription in a host plant cell.

By "promoter" is meant a sequence of nucleotides from which transcription may be initiated of DNA operably linked downstream (i.e. in the 3' direction on the sense strand of double-stranded DNA).

"Operably linked" means joined as part of the same nucleic acid molecule, suitably positioned and oriented for transcription to be initiated from the promoter. DNA operably linked to a promoter is "under transcriptional initiation regulation" of the promoter.

Suitable promoters which operate in plants include the Cauliflower Mosaic Virus 35S (CaMV 35S). Other examples are disclosed at pg 120 of Lindsey & Jones (1989) "Plant Biotechnology in Agriculture" Pub. OU Press, Milton Keynes, UK. The promoter may be selected to include one or more sequence motifs or elements conferring developmental and/or tissue-specific regulatory control of expression. Inducible plant promoters include the ethanol induced promoter of Caddick et al (1998) Nature Biotechnology 16 177-180.

Particularly of interest in the present context are nucleic acid constructs which operate as plant vectors. Specific procedures and vectors previously used with wide success upon plants are described by Guerineau and Mullineaux (1993) (Plant transformation and expression vectors. In: Plant Molecular Biology Labfax (Croy RRD ed) Oxford, BIOS Scientific Publishers, pp 121-148). Suitable vectors may include plant viral-derived vectors (see e.g. EP-A-194809).

Accordingly, the vector may comprise a nucleic acid sequence encoding EFR (including a nucleic acid sequence encoding a variant or fragment thereof), suitable for introducing an siRNA into the cell in any of the ways known in the art, for example, as described in any of references cited herein, which references are specifically incorporated herein by reference.

In one embodiment, the vector may comprise a nucleic acid sequence according to the invention in both the sense and antisense orientation, such that when expressed as RNA the sense and antisense sections will associate to form a double stranded RNA. This may for example be a long double stranded RNA (e.g., more than 23 nts) which may be processed in the cell to produce siRNAs (see for example Myers (2003) *Nature Biotechnology* 21:324-328).

Alternatively, the double stranded RNA may directly encode the sequences which form the siRNA duplex, as described above. In another embodiment, the sense and anti-sense sequences are provided on different vectors.

These vectors and RNA products may be useful for example to inhibit de novo production of the EFR polypeptide in a cell.

Thus the present invention provides, inter alia:

Double-stranded RNA which comprises an RNA sequence encoding EFR, an EFR homologue, or a fragment thereof, wherein EFR has the amino acid sequence set out in FIG. 5B.

Double-stranded RNA as above which is a siRNA duplex consisting of between 20 and 25 bps.

A vector encoding the dsRNA or siRNA duplex as described above. A method of producing the siRNA duplex above, the method comprising introducing the vector of claim into a host cell and causing or allowing transcription from the vector in the cell.

A method of producing the siRNA duplex above, the method comprising introducing, (i) a vector encoding the sense sequence of the siRNA duplex, and (ii) a vector encoding the anti-sense sequence of the siRNA duplex, into a host cell and causing or allowing transcription from the vectors in the cell. Also provided are methods of methods of enhancing the efficiency of the transformation of a plant by a bacterium which comprises suppressing EFR expression in the plant, for example by causing or allowing expression of the RNA or vectors described within the cells of the plant. The present invention further provides the use of a variant EFR or EFR fragment-encoding nucleotide sequence, or its complement, for down-regulation of gene expression, particularly down-regulation of expression of the EFR-encoding gene or homologue thereof, preferably in order to enhance the efficiency the transformation of the plant by a bacterium.

Plant Cells

In a further aspect of the invention, there is disclosed a host cell containing a heterologous construct as described above according to the present invention, especially a plant cell. The host cell (e.g. plant cell) is preferably transformed by the construct, which is to say that the construct becomes established within the cell, altering one or more of the cell's characteristics and hence phenotype e.g. with respect to the efficiency the transformation of the plant by a bacterium. Such plants may have an introduced lesion into the EFR gene, or it may be otherwise suppressed or silenced by the introduced nucleic acid.

The invention further encompasses a host cell transformed with nucleic acid or a vector according to the present invention (e.g. comprising a sequence capable of suppressing EFR expression) especially a plant cell.

Generally speaking, following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants, Vol I, II and III, Laboratory Procedures and Their Applications*, Academic Press, 1984, and Weissbach and Weissbach, *Methods for Plant Molecular Biology*, Academic Press, 1989.

The generation of fertile transgenic plants has been achieved in the cereals rice, maize, wheat, oat, and barley (reviewed in Shimamoto, K. (1994) *Current Opinion in Biotechnology* 5, 158-162.; Vasil, et al., (1992) *Bio/Technology* 10, 667-674; Vain et al., 1995, *Biotechnology Advances* 13 (4): 653-671; Vasil, 1996, *Nature Biotechnology* 14 page 702).

Plants which include a plant cell according to the invention are also provided.

In addition to the regenerated plant, the present invention embraces all of the following: a clone of such a plant, seed, selfed or hybrid progeny and descendants (e.g. F1 and F2 descendents).

Variants

Wherever a nucleotide or polypeptide sequence is referred to herein, unless context demands otherwise, it will be understood that functional variants of that sequence (or its complement depending on context) may be employed.

Identity between the sequence of FIG. 5B (or sequence encoding it) and the homologue may be at the nucleotide sequence and/or encoded amino acid sequence level. Preferably, the nucleic acid and/or amino acid sequence shares at least about 60%, or 70%, or 80% identity, most preferably at least about 90%, 95%, 96%, 97%, 98% or 99% identity.

Identity may be over the full-length of the relevant sequence shown herein, or may be over a part of it, preferably over a contiguous sequence of about or greater than about 20, 25, 30, 33, 40, 50, 67, 133, 167, 200, 233, 267, 300, 333, 400 or more amino acids or codons, compared with FIG. 6 or 5 respectively.

In addition to one or more changes within the amino acid sequence shown, a variant polypeptide may include additional amino acids at the C-terminus and/or N-terminus. Naturally, changes to the nucleic acid which make no difference to the encoded polypeptide (i.e. 'degeneratively equivalent') are included.

The percent identity of two amino acid or two nucleic acid sequences can be determined by visual inspection and mathematical calculation, or more preferably, the comparison is done by comparing sequence information using a computer program.

An exemplary, preferred computer program is the Genetics Computer Group (GCG; Madison, Wis.) Wisconsin package version 10.0 program, 'GAP' (Devereux et al., 1984, Nucl. Acids Res. 12: 387). The preferred default parameters for the 'GAP' program includes: (1) The GCG implementation of a unary comparison matrix (containing a value of 1 for identities and 0 for non-identities) for nucleotides, and the weighted amino acid comparison matrix of Gribskov and Burgess, Nucl. Acids Res. 14:6745, 1986, as described by Schwartz and Dayhoff, eds., Atlas of Polypeptide Sequence and Structure, National Biomedical Research Foundation, pp. 353-358, 1979; or other comparable comparison matrices; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps; and (4) no maximum penalty for long gaps.

REFERENCE LIST

Akira, S, and Takeda, K. (2004). Toll-like receptor signalling. Nat. Rev. Immunol. 4, 499-511.

Alonso, J. M., Stepanova, A. N., Leisse, T. J., Kim, C. J., Chen, H., Shinn, P., Stevenson, D. K., Zimmerman, J., Barajas, P., Cheuk, R., Gadrinab, C., Heller, C., Jeske, A., Koesema, E., Meyers, C. C., Parker, H., Prednis, L., Ansari, Y., Choy, N., Deen, H., Geralt, M., Hazari, N., Hom, E., Karnes, M., Mulholland, C., Ndubaku, R., Schmidt, I., Guzman, P., Aguilar-Henonin, L., Schmid, M., Weigel, D., Carter, D. E., Marchand, T., Risseeuw, E., Brogden, D., Zeko, A., Crosby, W. L., Berry, C. C., and Ecker, J. R. (2003). Genome-wide insertional mutagenesis of *Arabidopsis thaliana*. Science 301, 653-657.

Andersen-Nissen, E., Smith, K. D., Strobe, K. L., Barrett, S. L., Cookson, B. T., Logan, S. M., and Aderem, A. (2005). Evasion of Toll-like receptor 5 by flagellated bacteria. Proc. Natl. Acad. Sci. U.S. A 102, 9247-9252.

Asai, T., Tena, G., Plotnikova, J., Willmann, M. R., Chiu, W. L., Gómez-Gómez, L., Boller, T., Ausubel, F. M., and Sheen, J. (2002). MAP kinase signalling cascade in *Arabidopsis* innate immunity. Nature 415, 977-983.

Ausubel, F. M. (2005). Are innate immune signaling pathways in plants and animals conserved? Nat. Immunol. 6, 973-979.

Bauer, Z., Gómez-Gómez, L., Boller, T., and Felix, G. (2001). Sensitivity of different ecotypes and mutants of *Arabidopsis thaliana* toward the bacterial elicitor flagellin correlates with the presence of receptor-binding sites. J. Biol. Chem. 276, 45669-45676.

Bent, A. F., Innes, R. W., Ecker, J. R., and Staskawicz, B. J. (1992). Disease development in ethylene-insensitive *Arabidopsis thaliana* infected with virulent and avirulent *Pseudomonas* and *Xanthomonas* pathogens. Mol. Plant-Microbe Interact. 5, 372-378.

Bohnert, H. U., Fudal, I., Dioh, W., Tharreau, D., Notteghem, J. L., and Lebrun, M. H. (2004). A putative polyketide synthase/peptide synthetase from *Magnaporthe grisea* signals pathogen attack to resistant rice. Plant Cell 16, 2499-2513.

BROOKS, D. M., BENDER, C. L., and KUNKEL, B. N. (2005). The *Pseudomonas syringae* phytotoxin coronatine promotes virulence by overcoming salicylic acid-dependent defences in *Arabidopsis thaliana*. Molecular Plant Pathology 6, 629-639.

Brooks, D. M., Hernandez-Guzman, G., Kloek, A. P., Alarcon-Chaidez, F.,

Sreedharan, A., Rangaswamy, V., Penaloza-Vazquez, A., Bender, C. L., and Kunkel, B. N. (2004). Identification and characterization of a well-defined series of coronatine biosynthetic mutants of *Pseudomonas syringae* pv. tomato DC3000. Molecular Plant-Microbe Interactions 17, 162-174.

Broothaerts, W., Mitchell, H. J., Weir, B., Kaines, S., Smith, L. M., Yang, W., Mayer, J. E., Roa-Rodriguez, C., and Jefferson, R. A. (2005). Gene transfer to plants by diverse species of bacteria. Nature 433, 629-633.

Chen, Z. Y., Kloek, A. P., Boch, J., Katagiri, F., and Kunkel, B. N. (2000). The *Pseudomonas syringae* avrRpt2 gene product promotes pathogen virulence from inside plant cells. Molecular Plant-Microbe Interactions 13, 1312-1321.

Chinchilla, D., Bauer, Z., Regenass, M., Boller, T., and Felix, G. (2006). The *Arabidopsis* receptor kinase FLS2 binds flg22 and determines specificity of flagellin perception. Plant Cell in press.

Collmer, A., Badel, J. L., Charkowski, A. O., Deng, W. L., Fouts, D. E., Ramos, A. R., Rehm, A. H., Anderson, D. M., Schneewind, O., van Dijk, K., and Alfano, J. R. (2000). *Pseudomonas syringae* Hrp type III secretion system and effector proteins. Proceedings of the National Academy of Sciences of the United States of America 97, 8770-8777.

Dallo, S. F., Kannan, T. R., Blaylock, M. W., and Baseman, J. B. (2002). Elongation factor Tu and E1 beta subunit of pyruvate dehydrogenase complex act as fibronectin binding proteins in *Mycoplasma pneumoniae*. Mol. Microbiol. 46, 1041-1051.

Dangl, J. L., and Jones, J. D. (2001). Plant pathogens and integrated defence responses to infection. Nature 411, 826-833.

Deakin, W. J., Parker, V. E., Wright, E. L., Ashcroft, K. J., Loake, G. J., and Shaw, C. H. (1999). *Agrobacterium tumefaciens* possesses a fourth flagelin gene located in a large gene cluster concerned with flagellar structure, assembly and motility. Microbiology 145 (Pt 6), 1397-1407.

Dievart, A. and Clark, S. E. (2003). Using mutant alleles to determine the structure and function of leucine-rich repeat receptor-like kinases. Curr. Opin. Plant Biol. 6, 507-516.

Ditt, R. F., Nester, E., and Comai, L. (2005). The plant cell defense and *Agrobacterium tumefaciens*. FEMS Microbiol. Lett. 247, 207-213.

Ditt, R. F., Nester, E. W., and Comai, L. (2001). Plant gene expression response to *Agrobacterium tumefaciens*. Proc. Natl. Acad. Sci. U.S. A 98, 10954-10959.

Escobar, M. A. and Dandekar, A. M. (2003). *Agrobacterium tumefaciens* as an agent of disease. Trends Plant Sci. 8, 380-386.

Espinosa, A. and Alfano, J. R. (2004). Disabling surveillance: bacterial type III secretion system effectors that suppress innate immunity. Cell Microbiol. 6, 1027-1040.

Felix, G., Duran, J. D., Volko, S., and Boller, T. (1999). Plants have a sensitive perception system for the most conserved domain of bacterial flagellin. Plant J. 18, 265-276.

Fliegmann, J., Mithofer, A., Wanner, G., and Ebel, J. (2004). An ancient enzyme domain hidden in the putative beta-glucan elicitor receptor of soybean may play an active part in the perception of pathogen-associated molecular patterns during broad host resistance. J. Biol. Chem. 279, 1132-1140.

Gaffney, T., Friedrich, L., Vernooij, B., Negroto, D., Nye, G., Uknes, S., Ward, E., Kessmann, H., and Ryals, J. (1993). Requirement of salicylic acid for the induction of systemic acquired resistance. Science 261, 754-756.

Gasteiger, E., Gattiker, A., Hoogland, C., Ivanyi, I., Appel, R. D., and Bairoch, A. (2003). ExPASy: The proteomics server for in-depth protein knowledge and analysis. Nucleic Acids Res. 31, 3784-3788.

Gelvin, S. B. (2003). *Agrobacterium*-mediated plant transformation: the biology behind the "gene-jockeying" tool. Microbiol. Mol. Biol. Rev. 67, 16-37, table.

Gerber, I. B. and Dubery, I. A. (2004). Protein phosphorylation in *Nicotiana tabacum* cells in response to perception of lipopolysaccharides from *Burkholderia cepacia*. Phytochemistry 65, 2957-2966.

Glazebrook, J. (2005). Contrasting mechanisms of defense against biotrophic and necrotrophic pathogens. Annu Rev Phytopathol 43, 205-227.

Glickmann, E., Gardan, L., Jacquet, S., Hussain, S., Elasri, M., Petit, A., and Dessaux, Y. (1998). Auxin production is a common feature of most pathovars of *Pseudomonas syringae*. Mol Plant Microbe Interact 11, 156-162.

Gómez-Gómez, L. and Boller, T. (2000). FLS2: an LRR receptor-like kinase involved in the perception of the bacterial elicitor flagellin in *Arabidopsis*. Mol. Cell. 5, 1003-1011.

Gómez-Gómez, L., Felix, G., and Boller, T. (1999). A single locus determines sensitivity to bacterial flagellin in *Arabidopsis thaliana*. Plant J. 18, 277-284.

Granato, D., Bergonzelli, G. E., Pridmore, R. D., Marvin, L., Rouvet, M., and Corthesy-Theulaz, I. E. (2004). Cell surface-associated elongation factor Tu mediates the attachment of *Lactobacillus johnsonii* NCC533 (La1) to human intestinal cells and mucins. Infect. Immun. 72, 2160-2169.

Hanks, S. K. and Quinn, A. M. (1991). Protein kinase catalytic domain sequence database: identification of conserved features of primary structure and classification of family members. Methods Enzymol. 200, 38-62.

Hauck, P., Thilmony, R., and He, S. Y. (2003). A *Pseudomonas syringae* type III effector suppresses cell wall-based extracellular defense in susceptible *Arabidopsis* plants. Proceedings of the National Academy of Sciences of the United States of America 100, 8577-8582.

Hawn, T. R., Verbon, A., Letting a, K. D., Zhao, L. P., Li, S. S., Laws, R. J., Skerrett, S. J., Beutler, B., Schroeder, L., Nachman, A., Ozinsky, A., Smith, K. D., and Aderem, A. (2003). A common dominant TLR5 stop codon polymorphism abolishes flagellin signaling and is associated with susceptibility to legionnaires' disease. J. Exp. Med. 198, 1563-1572.

Hellens, R. P., Edwards, E. A., Leyland, N. R., Bean, S., and Mullineaux, P. M. (2000). pGreen: a versatile and flexible binary Ti vector for *Agrobacterium*-mediated plant transformation. Plant Mol. Biol. 42, 819-832.

Huang, H. C., Schuurink, R., Denny, T. P., Atkinson, M. M., Baker, C. J., Yucel, I., Hutcheson, S. W., and Collmer, A. (1988). Molecular cloning of a *Pseudomonas syringae* pv. *syringae* gene cluster that enables *Pseudomonas fluorescens* to elicit the hypersensitive response in tobacco plants. J Bacteriol 170, 4748-4756.

Jaffe M. J., Leopold A C (1984) Callose deposition during gravitropism of Zea mays and Pisum sativum and its inhibition by 2-deoxy-D-glucose. Planta 161: 20-26

Jeppesen, M. G., Navratil, T., Spremulli, L. L., and Nyborg, J. (2005). Crystal structure of the bovine mitochondrial elongation factor Tu.Ts complex. J. Biol. Chem. 280, 5071-5081.

Joh, L. D., Wroblewski, T., Ewing, N. N., and VanderGheynst, J. S. (2005). High-level transient expression of recombinant protein in lettuce. Biotechnol. Bioeng. 91, 861-871.

Jones, D. A. and Takemoto, D. (2004). Plant innate immunity—direct and indirect recognition of general and specific pathogen-associated molecules. Curr. Opin. Immunol. 16, 48-62.

Kazemi-Pour, N., Condemine, G., and Hugouvieux-Cotte-Pattat, N. (2004). The secretome of the plant pathogenic bacterium Erwinia chrysanthemi. Proteomics. 4, 3177-3186.

Kim, M. G., da, C. L., McFall, A. J., Belkhadir, Y., DebRoy, S., Dangl, J. L., and Mackey, D. (2005). Two Pseudomonas syringae type III effectors inhibit $RIN^4$-regulated basal defense in Arabidopsis. Cell 121, 749-759.

Kunze, G., Zipfel, C., Robatzek, S., Niehaus, K., Boller, T., and Felix, G. (2004). The N terminus of bacterial elongation factor Tu elicits innate immunity in Arabidopsis plants. Plant Cell 16, 3496-3507.

Matsubayashi, Y. and Sakagami, Y. (2000). 120- and 160-kDa receptors for endogenous mitogenic peptide, phytosulfokine-alpha, in rice plasma membranes. J. Biol. Chem. 275, 15520-15525.

Medzhitov, R. and Janeway, C. A. Jr. (2002). Decoding the patterns of self and nonself by the innate immune system. Science 296, 298-300.

Meindl, T., Boller, T., and Felix, G. (1998). The plant wound hormone systemin binds with the N-terminal part to its receptor but needs the C-terminal part to activate it. Plant Cell 10, 1561-1570.

Nakagami, H., Pitzschke, A., and Hirt, H. (2005). Emerging MAP kinase pathways in plant stress signalling. Trends Plant Sci. 10, 339-346.

Navarro, L., Zipfel, C., Rowland, O., Keller, I., Robatzek, S., Boiler, T., and Jones, J. D. G. (2004). The Transcriptional Innate Immune Response to flg22. Interplay and Overlap with Avr Gene-Dependent Defense Responses and Bacterial Pathogenesis. Plant Physiol 135, 1113-1128.

Nelson, P. E., Desjardins, A. E., and Plattner, R. D. (1993). Fumonisins, Mycotoxins Produced by Fusarium Species: Biology, Chemistry, and Significance. Annual Review of Phytopathology 31, 233-252.

Nimchuk, Z., Eulgem, T., Holt, B. F., III, and Dangl, J. L. (2003). Recognition and response in the plant immune system. Annu. Rev. Genet. 37, 579-609.

Nomura, K., Melotto, M., and He, S. Y. (2005). Suppression of host defense in compatible plant-Pseudomonas syringae interactions. Curr. Opin. Plant Biol. 8, 361-368.

Nühse, T. S., Peck, S. C., Hirt, H., and Boller, T. (2000). Microbial elicitors induce activation and dual phosphorylation of the Arabidopsis thaliana MAPK 6. J. Biol. Chem. 275, 7521-7526.

Nürnberger, T., Brunner, F., Kemmerling, B., and Piater, L. (2004). Innate immunity in plants and animals: striking similarities and obvious differences. Immunol. Rev. 198, 249-266.

O'Donnell, P. J., Schmeiz, E. A., Moussatche, P., Lund, S. T., Jones, J. B., and Klee, H. J. (2003). Susceptible to intolerance—a range of hormonal actions in a susceptible Arabidopsis pathogen response. PJ 33, 245-257.

Pfund, C., Tans-Kersten, J., Dunning, F. M., Alonso, J. M., Ecker, J. R., Allen, C., and Bent, A. F. (2004). Flagellin is not a major defense elicitor in Ralstonia solanacearum cells or extracts applied to Arabidopsis thaliana. Mol. Plant. Microbe Interact. 17, 696-706.

Post, D., Zhang, D., Eastvold, J. S., Teghanemt, A., Gibson, B. W., and Weiss, J. P. (2005). Biochemical and functional characterization of membrane blebs purified from Neisseria meningitidis serogroup B. J. Biol. Chem.

Preston, G. M., Studholme, D. J., and Caldelari, I. (2005). Profiling the secretomes of plant pathogenic Proteobacteria. FEMS Microbiol Rev 29, 331-360.

Ramos, H. C., Rumbo, M., and Sirard, J. C. (2004). Bacterial flagellins: mediators of pathogenicity and host immune responses in mucosa. Trends Microbiol. 12, 509-517.

Ritter, C., and Dangl, J. L. (1995). The avrRpm1 gene of Pseudomonas syringae pv. maculicola is required for virulence on Arabidopsis. MolPlant-Microbe Interact 8, 444-453.

Ron, M. and Avni, A. (2004). The receptor for the fungal elicitor ethylene-inducing xylanase is a member of a resistance-like gene family in tomato. Plant Cell 16, 1604-1615.

Scheer, J. M. and Ryan, C. A. (2002). The systemin receptor SR160 from Lycopersicon peruvianum is a member of the LRR receptor kinase family. Proc. Natl. Acad. Sci. U.S.A 99, 9585-9590.

Shaked, H., Melamed-Bessudo, C., and Levy, A. A. (2005). High-frequency gene targeting in Arabidopsis plants expressing the yeast RAD54 gene. PNAS102, 12265-12269.

Shiu, S. H. and Bleecker, A. B. (2001a). Receptor-like kinases from Arabidopsis form a monophyletic gene family related to animal receptor kinases. Proc. Natl. Acad. Sci. U.S. A 98, 10763-10768.

Shiu, S. H. and Bleecker, A. B. (2001b). Plant receptor-like kinase gene family: diversity, function, and signaling. Sci. STKE. 2001, RE22.

Shiu, S. H., Karlowski, W. M., Pan, R., Tzeng, Y. H., Mayer, K. F., and Li, W. H. (2004). Comparative analysis of the receptor-like kinase family in Arabidopsis and rice. Plant Cell 16, 1220-1234.

Singh, P., Piotrowski, M., Kloppstech, K., and Gau, A. E. (2004). Investigations on epiphytic living Pseudomonas species from Malus domestica with an antagonistic effect to Venturia inaequalis on isolated plant cuticle membranes. Environ. Microbiol. 6, 1149-1158.

Slade, A. J., and Knauf, V. C. (2005). TILLING moves beyond functional genomics into crop improvement. Transgenic Research 14, 109-115.

Suzuki, K. and Shinshi, H. (1995). Transient activation and tyrosine phosphorylation of a protein kinase in tobacco cells treated with a fungal elicitor. Plant Cell 7, 639-647.

Ton J, Mauch-Mani B (2004). b-Amino-butyric acid-induced resistance against necrotrophic pathogens is based on ABA-dependent priming for callose. Plant J 38: 119-130

Tzfira, T., Li, J., Lacroix, B., and Citovsky, V. (2004). Agrobacterium T-DNA integration: molecules and models. Trends Genet. 20, 375-383.

Umemoto, N., Kakitani, M., Iwamatsu, A., Yoshikawa, M., Yamaoka, N., and Ishida, I. (1997). The structure and function of a soybean beta-glucan-elicitor-binding protein. Proc. Natl. Acad. Sci. USA 94, 1029-1034.

Van der Hoorn, R. A., Laurent, F., Roth, R., and De Wit, P. J. (2000). Agroinfiltration is a versatile tool that facilitates comparative analyses of Avr9/Cf-9-induced and Avr4/Cf-4-induced necrosis. Mol. Plant. Microbe Interact. 13, 439-446.

van Wees, S. C. M., and Glazebrook, J. (2003). Loss of non-host resistance of *Arabidopsis* NahG to *Pseudomonas syringae* pv. *phaseolicola* is due to degradation products of salicylic acid. PJ 33, 733-742.

Veena, Jiang, H., Doerge, R. W., and Gelvin, S. B. (2003). Transfer of T-DNA and Vir proteins to plant cells by *Agrobacterium tumefaciens* induces expression of host genes involved in mediating transformation and suppresses host defense gene expression. Plant J. 35, 219-236.

Wan J., Zhang S., and Stacey, G. (2004). Activation of a mitogen-activated protein kinase pathway in *Arabidopsis* by chitin. Mol Plant Pathol 5 (2), 125-135.

Watt, S. A., Wilke, A., Patschkowski, T., and Niehaus, K. (2005). Comprehensive analysis of the extracellular proteins from *Xanthomonas campestris* pv. *campestris* B100. Proteomics. 5, 153-167.

Wroblewski, T., Tomczak, A., and Michelmore, R. (2005). Optimization of *Agrobacterium*-mediated transient assays of gene expression in lettuce, tomato and *Arabidopsis*. Plant Biotechnology Journal 3, 259-273.

Xu, X. Q., Li, L. P., and Pan, S. Q. (2001). Feedback regulation of an *Agrobacterium* catalase gene katA involved in *Agrobacterium*-plant interaction. Mol Microbiol 42, 645-657.

Xu, X. Q., and Pan, S. Q. (2000). An *Agrobacterium* catalase is a virulence factor involved in tumorigenesis. Mol Microbiol 35, 407-414.

Yarovinsky, F., Zhang, D., Andersen, J. F., Bannenberg, G. L., Serhan, C. N., Hayden, M. S., Hieny, S., Sutterwala, F. S., Flavell, R. A., Ghosh, S., and Sher, A. (2005). TLR11 activation of dendritic cells by a protozoan profilin-like protein. Science 308, 1626-1629.

Yun, B. W., Atkinson, H. A., Gaborit, C., Greenland, A., Read, N. D., Pallas, J. A., and Loake, G. J. (2003). Loss of actin cytoskeletal function and EDS1 activity, in combination, severely compromises non-host resistance in *Arabidopsis* against wheat powdery mildew. Plant J 34, 768-777.

Yun et al. (2006) Suppression of Plant Defense Responses. Plant Physiology Preview. Published on Mar. 10, 2006, as O1:10. 1104/pp. 105.074542.

Zhang, D., Zhang, G., Hayden, M. S., Greenblatt, M. B., Bussey, C., Flavell, R. A., and Ghosh, S. (2004). A toll-like receptor that prevents infection by uropathogenic bacteria. Science 303, 1522-1526.

Zhu, Y., Nam, J., Humara, J. M., Mysore, K. S., Lee, L. Y., Cao, H., Valentine, L., Li, J., Kaiser, A. D., Kopecky, A. L., Hwang, H. H., Bhattacharjee, S., Rao, P. K., Tzfira, T., Rajagopal, J., Yi, H., Veena, Yadav, B. S., Crane, Y. M., Lin, K., Larcher, Y., Gelvin, M. J., Knue, M., Ramos, C., Zhao, X., Davis, S. J., Kim, S. I., Ranjith-Kumar, C. T., Choi, Y. J., Hallan, V. K., Chattopadhyay, S., Sui, X., Ziemienowicz, A., Matthysse, A. G., Citovsky, V., Hohn, B., and Gelvin, S. B. (2003). Identification of *Arabidopsis* rat mutants. Plant Physiol 132, 494-505.

Zimmermann, P., Hirsch-Hoffmann, M., Hennig, L., and Gruissem, W. (2004). GENEVESTIGATOR. *Arabidopsis* microarray database and analysis toolbox. Plant Physiol. 136, 2621-2632.

Zipfel, C. and Felix, G. (2005). Plants and animals: a different taste for microbes? Curr. Opin. Plant Biol. 8, 353-360.

Zipfel, C., Robatzek, S., Navarro, L., Oakeley, E. J., Jones, J. D., Felix, G., and Boller, T. (2004). Bacterial disease resistance in *Arabidopsis* through flagellin perception. Nature 428, 764-767.

Zipfel, C., and Felix, G. (2005). Plants and animals: a different taste for microbes? Current Opinion in Plant Biology 8, 1-8.

---

What is claimed is:

1. A method for enhancing efficiency of transformation of a plant by a bacterium comprising: reducing or eliminating expression of EF-Tu receptor (EFR) in said plant, wherein said EF-Tu receptor comprises an amino acid sequence selected from the group consisting of: SEQ ID NO: 1; a sequence having at least 95%, identity to SEQ ID NO: 1: a sequence having at least 98% identity to SEQ ID NO: 1; and a sequence having at least 99% identity to SEQ ID NO: 1.

2. The method according to claim 1 wherein said bacterium is *Agrobacterium*.

3. The method according to claim 1, wherein said plant further comprises at least one gene selected from the group consisting of: nahG, sid2, eds5, pad4, pad2, ndr1, and eds1.

4. The method according to claim 1, further comprising transiently transforming said plant with a mixed inoculation of *Agrobacterium* carrying at least one gene that encodes an effector selected from the group consisting of: nahG; avrPto; avrRpm1; AvrRpt2; and combinations thereof.

5. The method according to claim 4, comprising mixed or sequential exposure of plant cells to *Agrobacterium* strains carrying the at least one gene that encodes the effector, and strains that transform a plant variety with a gene of interest.

6. The method according to claim 4, wherein two compatible binary plasmids are situated in the same *Agrobacterium* strain, so that transformation of T-DNAs carrying the at least one gene that encodes the effector and T-DNAs carrying a gene of interest occurs in parallel.

7. The method according to claim 6, further comprising: selecting, via different antibiotic resistance, transformed plants in which the gene of interest has been stably delivered and in which the at least one gene that encodes the effector has segregated away via Mendelian inheritance.

8. The method according to claim 1, further comprising applying at least one natural or synthetic chemical to suppress plant defenses.

9. The method according to claim 8, wherein said natural or synthetic chemical is selected from the group consisting of: catechol; jasmonate; coronatine; mycotoxins; an avirulence gene in the rice blast pathogen *Magnaporthe grisea*, which encodes a polyketide synthase; cytochalasin E; auxin; and combinations thereof.

10. The method according to claim 9 wherein said jasmonate is MeJA, and said mycotoxin is selected from Fumonisin S made by *Fusarium moniliforme*, and deoxynivalenol (DON) made by *Fusarium* and *Aspergillus* species.

11. The method according to claim 1 wherein the bacterium is *A. tumefaciens* having a functional type IV secretion system.

12. The method according to claim 1, wherein the bacterium is an *Agrobacteria* and the bacterium is co-inoculated with other bacteria that suppress host defense in sequential and/or mixed infections.

13. The method according to claim 1, further comprising the step of subsequently contacting the plant with the bacterium, wherein the bacterium carries a gene of interest.

14. The method of claim 1, wherein the plant is *Arabidopsis*.

* * * * *

UNITED STATES PATENT AND TRADEMARK OFFICE
CERTIFICATE OF CORRECTION

| | | |
|---|---|---|
| PATENT NO. | : 8,232,452 B2 | |
| APPLICATION NO. | : 12/097256 | |
| DATED | : July 31, 2012 | |
| INVENTOR(S) | : Cyril Zipfel et al. | |

It is certified that error appears in the above-identified patent and that said Letters Patent is hereby corrected as shown below:

| Col. No. | Line(s) | Edits |
|---|---|---|
| 48 | 52 | Replace "nisin S made by" with --nisin B made by-- |

Signed and Sealed this
Twenty-third Day of October, 2012

David J. Kappos
*Director of the United States Patent and Trademark Office*

SEQUENCE LISTING

<160> NUMBER OF SEQ ID NOS: 9

<210> SEQ ID NO 1
<211> LENGTH: 1027
<212> TYPE: PRT
<213> ORGANISM: Arabidopsis thaliana

<400> SEQUENCE: 1

```
Met Lys Leu Ser Phe Ser Leu Val Phe Asn Ala Leu Thr Leu Leu Leu
1               5                   10                  15

Gln Val Cys Ile Phe Ala Gln Ala Arg Phe Ser Asn Glu Thr Asp Met
            20                  25                  30

Gln Ala Leu Leu Glu Phe Lys Ser Gln Val Ser Glu Asn Asn Lys Arg
        35                  40                  45

Glu Val Leu Ala Ser Trp Asn His Ser Ser Pro Phe Cys Asn Trp Ile
    50                  55                  60

Gly Val Thr Cys Gly Arg Arg Glu Arg Val Ile Ser Leu Asn Leu
65                  70                  75                  80

Gly Gly Phe Lys Leu Thr Gly Val Ile Ser Pro Ser Ile Gly Asn Leu
                85                  90                  95

Ser Phe Leu Arg Leu Leu Asn Leu Ala Asp Asn Ser Phe Gly Ser Thr
                100                 105                 110

Ile Pro Gln Lys Val Gly Arg Leu Phe Arg Leu Gln Tyr Leu Asn Met
            115                 120                 125
```

-continued

```
Ser Tyr Asn Leu Leu Glu Gly Arg Ile Pro Ser Ser Leu Ser Asn Cys
    130                 135                 140

Ser Arg Leu Ser Thr Val Asp Leu Ser Ser Asn His Leu Gly His Gly
145                 150                 155                 160

Val Pro Ser Glu Leu Gly Ser Leu Ser Lys Leu Ala Ile Leu Asp Leu
                165                 170                 175

Ser Lys Asn Asn Leu Thr Gly Asn Phe Pro Ala Ser Leu Gly Asn Leu
            180                 185                 190

Thr Ser Leu Gln Lys Leu Asp Phe Ala Tyr Asn Gln Met Arg Gly Glu
        195                 200                 205

Ile Pro Asp Glu Val Ala Arg Leu Thr Gln Met Val Phe Phe Gln Ile
210                 215                 220

Ala Leu Asn Ser Phe Ser Gly Phe Pro Pro Ala Leu Tyr Asn Ile
225                 230                 235                 240

Ser Ser Leu Glu Ser Leu Ser Leu Ala Asp Asn Ser Phe Ser Gly Asn
                245                 250                 255

Leu Arg Ala Asp Phe Gly Tyr Leu Leu Pro Asn Leu Arg Arg Leu Leu
            260                 265                 270

Leu Gly Thr Asn Gln Phe Thr Gly Ala Ile Pro Lys Thr Leu Ala Asn
        275                 280                 285

Ile Ser Ser Leu Glu Arg Phe Asp Ile Ser Ser Asn Tyr Leu Ser Gly
290                 295                 300

Ser Ile Pro Leu Ser Phe Gly Lys Leu Arg Asn Leu Trp Trp Leu Gly
305                 310                 315                 320

Ile Arg Asn Asn Ser Leu Gly Asn Asn Ser Ser Ser Gly Leu Glu Phe
                325                 330                 335

Ile Gly Ala Val Ala Asn Cys Thr Gln Leu Glu Tyr Leu Asp Val Gly
            340                 345                 350

Tyr Asn Arg Leu Gly Gly Glu Leu Pro Ala Ser Ile Ala Asn Leu Ser
        355                 360                 365

Thr Thr Leu Thr Ser Leu Phe Leu Gly Gln Asn Leu Ile Ser Gly Thr
370                 375                 380

Ile Pro His Asp Ile Gly Asn Leu Val Ser Leu Gln Glu Leu Ser Leu
385                 390                 395                 400

Glu Thr Asn Met Leu Ser Gly Glu Leu Pro Val Ser Phe Gly Lys Leu
                405                 410                 415

Leu Asn Leu Gln Val Val Asp Leu Tyr Ser Asn Ala Ile Ser Gly Glu
            420                 425                 430

Ile Pro Ser Tyr Phe Gly Asn Met Thr Arg Leu Gln Lys Leu His Leu
        435                 440                 445

Asn Ser Asn Ser Phe His Gly Arg Ile Pro Gln Ser Leu Gly Arg Cys
450                 455                 460

Arg Tyr Leu Leu Asp Leu Trp Met Asp Thr Asn Arg Leu Asn Gly Thr
465                 470                 475                 480

Ile Pro Gln Glu Ile Leu Gln Ile Pro Ser Leu Ala Tyr Ile Asp Leu
                485                 490                 495

Ser Asn Asn Phe Leu Thr Gly His Phe Pro Glu Glu Val Gly Lys Leu
            500                 505                 510

Glu Leu Leu Val Gly Leu Gly Ala Ser Tyr Asn Lys Leu Ser Gly Lys
        515                 520                 525

Met Pro Gln Ala Ile Gly Gly Cys Leu Ser Met Glu Phe Leu Phe Met
530                 535                 540

Gln Gly Asn Ser Phe Asp Gly Ala Ile Pro Asp Ile Ser Arg Leu Val
```

-continued

```
           545                 550                 555                 560
    Ser Leu Lys Asn Val Asp Phe Ser Asn Asn Leu Ser Gly Arg Ile
                        565                 570                 575
    Pro Arg Tyr Leu Ala Ser Leu Pro Ser Leu Arg Asn Leu Asn Leu Ser
                        580                 585                 590
    Met Asn Lys Phe Glu Gly Arg Val Pro Thr Thr Gly Val Phe Arg Asn
                        595                 600                 605
    Ala Thr Ala Val Ser Val Phe Gly Asn Thr Asn Ile Cys Gly Gly Val
                        610                 615                 620
    Arg Glu Met Gln Leu Lys Pro Cys Ile Val Gln Ala Ser Pro Arg Lys
    625                 630                 635                 640
    Arg Lys Pro Leu Ser Val Arg Lys Lys Val Ser Gly Ile Cys Ile
                        645                 650                 655
    Gly Ile Ala Ser Leu Leu Leu Ile Ile Ile Val Ala Ser Leu Cys Trp
                        660                 665                 670
    Phe Met Lys Arg Lys Lys Asn Asn Ala Ser Asp Gly Asn Pro Ser
                        675                 680                 685
    Asp Ser Thr Thr Leu Gly Met Phe His Glu Lys Val Ser Tyr Glu Glu
                        690                 695                 700
    Leu His Ser Ala Thr Ser Arg Phe Ser Ser Thr Asn Leu Ile Gly Ser
    705                                 710                 715                 720
    Asn Phe Gly Asn Val Phe Lys Gly Leu Leu Pro Glu Asn Lys Leu
                        725                 730                 735
    Val Ala Val Lys Val Leu Asn Leu Leu Lys His Gly Ala Thr Lys Ser
                        740                 745                 750
    Phe Met Ala Glu Cys Glu Thr Phe Lys Gly Ile Arg His Arg Asn Leu
                        755                 760                 765
    Val Lys Leu Ile Thr Val Cys Ser Ser Leu Asp Glu Gly Asn Asp Phe
                        770                 775                 780
    Arg Ala Leu Val Tyr Glu Phe Met Pro Lys Gly Ser Leu Asp Met Trp
    785                                 790                 795                 800
    Leu Gln Leu Glu Asp Leu Glu Arg Val Asn Asp His Ser Arg Ser Leu
                        805                 810                 815
    Thr Pro Ala Glu Lys Leu Asn Ile Ala Ile Asp Val Ala Ser Ala Leu
                        820                 825                 830
    Glu Tyr Leu His Val His His Asp Pro Val Ala His Cys Asp Ile Lys
                        835                 840                 845
    Pro Ser Asn Ile Leu Leu Asp Asp Leu Thr Ala His Val Ser Asp
                        850                 855                 860
    Phe Gly Leu Ala Gln Leu Leu Tyr Lys Tyr Asp Arg Glu Ser Phe Leu
    865                                 870                 875                 880
    Asn Gln Phe Ser Ser Ala Gly Val Arg Gly Thr Ile Gly Tyr Ala Ala
                        885                 890                 895
    Pro Tyr Gly Met Gly Gly Gln Pro Ser Ile Gln Gly Asp Val Tyr Ser
                        900                 905                 910
    Phe Gly Ile Leu Leu Leu Glu Met Phe Ser Gly Lys Glu Pro Thr Asp
                        915                 920                 925
    Glu Ser Phe Ala Gly Asp Tyr Asn Leu His Ser Tyr Thr Lys Ser Ile
                        930                 935                 940
    Leu Ser Gly Cys Thr Ser Ser Gly Gly Ser Asn Ala Ile Asp Glu Gly
    945                                 950                 955                 960
    Leu Arg Leu Val Leu Gln Val Gly Ile Lys Cys Ser Glu Glu Tyr Pro
                        965                 970                 975
```

-continued

```
Arg Asp Arg Met Arg Thr Asp Glu Ala Val Arg Glu Leu Ile Ser Ile
            980                 985                 990

Arg Ser Lys Phe Phe Ser Ser Lys  Thr Thr Ile Thr Glu  Ser Pro Arg
        995                 1000                1005

Asp Ala  Pro Gln Ser Ser Pro  Gln Glu Trp Met Leu  Asn Thr Asp
    1010                1015                1020

Met His  Thr Met
    1025

<210> SEQ ID NO 2
<211> LENGTH: 24
<212> TYPE: PRT
<213> ORGANISM: Artificial sequence
<220> FEATURE:
<223> OTHER INFORMATION: Synthetic sequence: Consensus sequence of
      leucine-rich repeat (LRR) domain
<220> FEATURE:
<221> NAME/KEY: misc_feature
<222> LOCATION: 2, 3, 5, 6, 8, 10, 11, 13, 15, 17, 20, 21, 24
<223> OTHER INFORMATION: Xaa = no overall consensus

<400> SEQUENCE: 2

Leu Xaa Xaa Leu Xaa Xaa Leu Xaa Leu Xaa Xaa Asn Xaa Leu Xaa Gly
1               5                   10                  15

Xaa Ile Pro Xaa Xaa Leu Gly Xaa
            20

<210> SEQ ID NO 3
<211> LENGTH: 21
<212> TYPE: DNA
<213> ORGANISM: Artificial Sequence
<220> FEATURE:
<223> OTHER INFORMATION: Synthetic sequence: Gene-specific forward
      primer for efr-1

<400> SEQUENCE: 3
gctgcagcca catatccaga c                                           21

<210> SEQ ID NO 4
<211> LENGTH: 22
<212> TYPE: DNA
<213> ORGANISM: Artificial Sequence
<220> FEATURE:
<223> OTHER INFORMATION: Synthetic sequence: Gene-specific reverse
      primer for efr-1

<400> SEQUENCE: 4
ggaagggtgc caacaacagg ag                                          22

<210> SEQ ID NO 5
<211> LENGTH: 18
<212> TYPE: DNA
<213> ORGANISM: Artificial Sequence
<220> FEATURE:
<223> OTHER INFORMATION: Synthetic sequence: Gene-specific forward
      primer for efr-2

<400> SEQUENCE: 5
ggattgcttg gccctgag                                               18

<210> SEQ ID NO 6
<211> LENGTH: 15
<212> TYPE: DNA
<213> ORGANISM: Artificial Sequence
<220> FEATURE:
<223> OTHER INFORMATION: Synthetic sequence: Gene-specific reverse
      primer for efr-2
```

```
<400> SEQUENCE: 6
actagtagtc tctcc                                                         15

<210> SEQ ID NO 7
<211> LENGTH: 22
<212> TYPE: DNA
<213> ORGANISM: Artificial Sequence
<220> FEATURE:
<223> OTHER INFORMATION: Synthetic sequence: T-DNA left border specific
      primer LBb1

<400> SEQUENCE: 7
gcgtggaccg cttgctgcaa ct                                                 22

<210> SEQ ID NO 8
<211> LENGTH: 33
<212> TYPE: DNA
<213> ORGANISM: Artificial Sequence
<220> FEATURE:
<223> OTHER INFORMATION: Synthetic sequence: Forward primer

<400> SEQUENCE: 8
ttaacccggg ggtggaacct gcatcatgta aac                                     33

<210> SEQ ID NO 9
<211> LENGTH: 37
<212> TYPE: DNA
<213> ORGANISM: Artificial Sequence
<220> FEATURE:
<223> OTHER INFORMATION: Synthetic sequence: Reverse primer

<400> SEQUENCE: 9
taatggtacc gccatagtat gcatgtccgt atttaac                                 37
```